US012359250B2

(12) United States Patent
Vogelstein et al.

(10) Patent No.: US 12,359,250 B2
(45) Date of Patent: Jul. 15, 2025

(54) BOTTLENECK SEQUENCING

(71) Applicant: The Johns Hopkins University, Baltimore, MD (US)

(72) Inventors: Bert Vogelstein, Baltimore, MD (US); Kenneth Kinzler, Baltimore, MD (US); Margaret Hoang, Baltimore, MD (US); Nickolas Papadopoulos, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 649 days.

(21) Appl. No.: 16/073,622

(22) PCT Filed: Jan. 27, 2017

(86) PCT No.: PCT/US2017/015229
§ 371 (c)(1),
(2) Date: Jul. 27, 2018

(87) PCT Pub. No.: WO2017/132438
PCT Pub. Date: Aug. 3, 2017

(65) Prior Publication Data
US 2019/0300946 A1    Oct. 3, 2019

Related U.S. Application Data
(60) Provisional application No. 62/288,869, filed on Jan. 29, 2016.

(51) Int. Cl.
| | | |
|---|---|---|
| C12Q 1/6869 | (2018.01) | |
| C12Q 1/68 | (2018.01) | |
| C12Q 1/6855 | (2018.01) | |
| C40B 20/04 | (2006.01) | |

(52) U.S. Cl.
CPC .......... *C12Q 1/6869* (2013.01); *C12Q 1/68* (2013.01); *C12Q 1/6855* (2013.01); *C40B 20/04* (2013.01); *C12Q 2600/156* (2013.01)

(58) Field of Classification Search
CPC ...... C12Q 1/6869; C12Q 1/68; C12Q 1/6855; C12Q 2600/156; C12Q 1/6844; C40B 20/04
See application file for complete search history.

(56) References Cited

U.S. PATENT DOCUMENTS

2016/0152972 A1*  6/2016  Stapleton et al. . C12N 15/1065
2016/0289753 A1* 10/2016  Osborne et al. ..... C12Q 1/6869

FOREIGN PATENT DOCUMENTS

| EP | 2719774 | 4/2014 | |
|---|---|---|---|
| WO | WO-2012142213 A2 * | 10/2012 | ........... C12Q 1/6806 |
| WO | WO2013142389 | 9/2013 | |

OTHER PUBLICATIONS

Albertini et al., "In vivo somatic mutations in humans: measurement and analysis.", Annu Rev Genet 24, 305-326, 1990.
Baslan et al., "Single cell sequencing approaches for complex biological systems", Current opinion in genetics & development 26, 59-65, 2014.
Cole et al., International Commission for Protection Against Environmental Mutagens and Carcinogens. Working paper No. 3. Somatic mutant frequency, mutation rates and mutational spectra in the human population in vivo. Mutat Res 304, 33-105, 1994.
Costello et al., "Discovery and characterization of artifactual mutations in deep coverage targeted capture sequencing data due to oxidative DNA damage during sample preparation.", Nucleic acids research 41, e67, 2013.
Hamilton et al., "The molecular basis of Turcot's syndrome.", The New England journal of medicine 332, 839-847, 1995.
Hiatt et al., "Single molecule molecular inversion probes for targeted, high-accuracy detection of low-frequency variation.", Genome research 23, 843-854, 2013.
Hoang et al., Mutational signature of aristolochic acid exposure as revealed by whole-exome sequencing. Science translational medicine 5, 197ra102, 2013.
International Search Report and Written Opinion in International Application No. PCT/US2017/015229, dated May 18, 2017, 7 pages.
Jabara et al., "Accurate sampling and deep sequencing of the HIV-1 protease gene using a Primer ID.", Proceedings of the National Academy of Sciences of the United States of America 108, 20166-20171, 2011.
Jiao et al., "DAXX/ATRX, MEN1, and mTOR pathway genes are frequently altered in pancreatic neuroendocrine tumors.", Science 331, 1199-1203, 2011.
Ju et al., "Origins and functional consequences of somatic mitochondrial DNA mutations in human cancer.", eLife 3, 28 pages, 2014.
Kandoth et al., Mutational landscape and significance across 12 major cancer types., Nature 502, 333-339, 2013.
Kennedy et al., "Somatic mutations in aging, cancer and neurodegeneration.", Mech Ageing Dev 133, 118-126, 2012.
Kennedy et al., "Ultra-sensitive sequencing reveals an age-related increase in somatic mitochondrial mutations that are inconsistent with oxidative damage.", PLoS Genet 9, e1003794, 2013.
Kennedy et al., Detecting ultralow-frequency mutations by Duplex Sequencing, Nature protocols 9, 2586-2606, 2014.

(Continued)

*Primary Examiner* — Nancy J Leith
*Assistant Examiner* — Jessica D Parisi
(74) *Attorney, Agent, or Firm* — Fish & Richardson P.C.

(57) ABSTRACT

Bottleneck Sequencing System (BotSeqS) is a next-generation sequencing method that simultaneously quantifies rare somatic point mutations across the mitochondrial and nuclear genomes. BotSeqS combines molecular barcoding with a simple dilution step immediately prior to library amplification. BotSeqS can be used to show age and tissue-dependent accumulations of rare mutations and demonstrate that somatic mutational burden in normal tissues can vary by several orders of magnitude, depending on biologic and environmental factors. BotSeqS has been used to show major differences between the mutational patterns of the mitochondrial and nuclear genomes in normal tissues. Lastly, BotSeqS has shown that the mutation spectra of normal tissues were different from each other, but similar to those of the cancers that arose in them.

11 Claims, 11 Drawing Sheets
Specification includes a Sequence Listing.

(56) References Cited

OTHER PUBLICATIONS

Keys et al., "Primer ID Informs Next-Generation Sequencing Platforms and Reveals Preexisting Drug Resistance Mutations in the HIV-1 Reverse Transcriptase Coding Domain.", AIDS Res Hum Retroviruses 31, 658-668, 2015.
Kinde et al. "Evaluation of DNA from the Papanicolaou test to detect ovarian and endometrial cancers.", Science translational medicine 5, 167ra164, 2013.
Kinde et al., "Detection and quantification of rare mutations with massively parallel sequencing.", Proceedings of the National Academy of Sciences of the United States of America 108, 9530-9535, 2011.
Kivioja et al., "Counting absolute number. of molecules using unique molecular identifiers", Nature Methods, 9, 72-74, 2012.
Kumar et al., "Deep sequencing of multiple regions of glial tumors reveals spatial heterogeneity for mutations in clinically relevant genes.", Genome biology 15, 530, 2014.
Li "Toward better understanding of artifacts in variant calling from highcoverage samples" Bioinformatics 30, 2843-2851, 2014.
Lodato et al., "Somatic mutation in single human neurons tracks developmental and transcriptional history.", Science 350, 94-98, 2015.
Madabhushi et al., "DNA damage and its links to neurodegeneration.", Neuron 83, 266-282, 2014.
Navin et al., "Tumour evolution inferred by single-cell sequencing.", Nature 472, 90-94, 2011.
Parsons et al., "Mismatch repair deficiency in phenotypically normal human cells.", Science 268, 738-740, 1995.
Randerath et al., "Covalent DNA damage in tissues of cigarette smokers as determined by 32P-postlabeling assay.", Journal of the National Cancer Institute 81, 341-347, 1989.
Ross et al., "Characterizing and measuring bias in sequence data.", Genome biology 14, R51, 20 pages, 2013.
Scheibye-Knudsen et al., "Protecting the mitochondrial powerhouse.", Trends in cell biology 25, 158-170, 2015.
Schmitt et al., "Detection of ultra-rare mutations by next-generation sequencing.", Proceedings of the National Academy of Sciences of the United States of America, 109, 14508-14513, 2012.
Schmitt et al., "Sequencing small genomic targets with high efficiency and extreme accuracy.", Nature methods 12, 423-425, 2015.
Shlien et al., "Combined hereditary and somatic mutations of replication error repair genes result in rapid onset of ultrahypermutated cancers.", Nature genetics 47, 257-262, 2015.
Spalding et al., "Retrospective birth dating of cells in humans", Cell 122, 133-143, 2005.
Stratton et al., "The cancer genome.", Nature 458, 719-724, 2009.
Tomasetti et al., "Variation in cancer risk among tissues can be explained by the number of stem cell divisions.", Science 347, 78-81, 2015.
Tomasetti et al., "Half or more of the somatic mutations in cancers of self-renewing tissues originate prior to tumor initiation.", Proceedings of the National Academy of Sciences of the United States of America 110, 1999-2004, 2013.
Vijg, "Somatic mutations, genome mosaicism, cancer and aging.", Current opinion in genetics & development 26, 141-149, 2014.
Wang et al., "Genome-wide single-cell analysis of recombination activity and de novo mutation rates in human sperm.", Cell 150, 402-412, 2012.
Zong et al., "Genome-wide detection of singlenucleotide and copy-number variations of a single human cell.", Science 338, 1622-1626, 2012.
De Vos et al., "Novel PMS2 pseudogenes can conceal recessive mutations causing a distinctive childhood cancer syndrome.", American journal of human genetics 74, 954-964, 2004.
Hoang et al., "Genome-wide quantification of rare somatic mutations in normal human tissues using massively parallel sequencing", PNAS 113(35): 9846-51, 2006.
Hoang et al., "Genome-wide quantification of rare somatic mutations in normal human tissues using massively parallel sequencing", PNAS 113(35): 9846-51, 2016.
International Preliminary Report on Patentability in Application No. PCT/US2017/015229, dated Jul. 31, 2018, 5 pages.

* cited by examiner

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: TS-PCR Oligo1

<400> SEQUENCE: 1
aatgatacgg cgaccaccga ga                                              22

<210> SEQ ID NO 2
<211> LENGTH: 22
<212> TYPE: DNA
<213> ORGANISM: Artificial Sequence
<220> FEATURE:
<223> OTHER INFORMATION: TS-PCR Oligo2

<400> SEQUENCE: 2
caagcagaag acggcatacg ag                                              22
```

BOTTLENECK SEQUENCING

This application is a National Stage application under 35 U.S.C. § 371 of International Application No. PCT/US2017/015229, having an International Filing Date of Jan. 27, 2017, which claims the benefit of priority of U.S. Provisional Application No. 62/288,869, filed Jan. 29, 2016, each of which is incorporated herein by reference in its entirety.

STATEMENT OF GOVERNMENTAL INTEREST

This invention was made with government support under CA057345, CA043460, and CA062924 awarded by the National Institutes of Health. The government has certain rights in the invention.

FIELD OF THE INVENTION

The present invention is related to the area of nucleic acid sequencing. In particular, it relates to identification and/or quantification of mutational load.

INCORPORATION-BY-REFERENCE OF MATERIAL SUBMITTED ELECTRONICALLY

This application contains a sequence listing. It has been submitted electronically via EFS-Web as an ASCII text file entitled "P13967-02 ST25.txt." The sequence listing is 593 bytes in size, and was created on Jan. 27, 2017. It is hereby incorporated by reference in its entirety

BACKGROUND OF THE INVENTION

The accumulation of random somatic mutations in the nuclear and mitochondrial genomes over time underlies fundamental theories of carcinogenesis, neurodegeneration, and aging[1-3]. Direct observation of these rare mutations in the human body with age therefore has the potential to enhance our understanding of human disease. Currently, no simple high-throughput method exists to directly and systematically quantify somatic mutational load in normal, non-diseased human tissues at a genome-wide level. Next-generation DNA sequencing (NGS) technologies are an ideal platform to address this issue, but their sequencing error rate limits the detection of rare mutations. For example, the Illumina platform has the lowest reported error rate, but even with sophisticated post-sequencing analysis, the sensitivity is at best 0.1%[4], far lower than required to detect rare mutations in normal human tissues[5, 6].

Two main NGS strategies have been developed for more sensitive detection of rare mutations: single cell genomic sequencing[7-9] and consensus sequencing with molecular barcodes[10-13]. Single cell genomic sequencing has the potential to detect rare mutations in a genome-wide fashion, with sensitivity achieved through the isolation of single cells from the bulk population. However, point mutations are introduced during whole-genome amplification of the picograms of DNA isolated from single cells. To increase the specificity of point mutation calling with single cell methods, it is necessary to identify the same point mutation in at least two different cells[14]. This approach, though useful for the evaluation of tumor heterogeneity and other purposes, cannot accurately call a point mutation that is private to a single cell. In contrast, consensus sequencing with molecular barcodes can accurately detect very rare point mutations ($<10^{-6}$) by distinguishing individual DNA molecules in a population with a unique barcode. This unique molecule identifier[15] is used to group reads from the same DNA template; only mutations that are present in most or all of the reads from the same template are scored as mutations[10-13]. Although sensitive and accurate, molecular barcoding methods are designed for targeted loci[16-18] or small, pre-defined genomic regions[19, 20] rather than unbiased detection across the human genome.

There is a continuing need in the art to accurately detect rare point mutations in any molecularly-barcoded library in a completely unbiased fashion. In addition, there is a need in the art for sensitive methods for studying somatic mutations in normal human tissues.

SUMMARY OF THE INVENTION

According to one aspect of the invention, a method is provided for obtaining the sequence of a DNA. Adaptors are ligated to ends of random fragments of a DNA population to form a library of adaptor-ligated fragments, such that upon amplification of a fragment in the library of adaptor-ligated fragments, each end of the fragment has a distinct end. The library of adaptor-ligated fragments is diluted to form diluted, adaptor-ligated fragments. At least a portion of the diluted, adaptor-ligated fragments is amplified to form families from a single strand of an adaptor-ligated fragment. Family members are sequenced to obtain nucleotide sequence of a plurality of family members of an adaptor-ligated fragment.

According to another aspect of the invention a method is provided for sequencing DNA. Adaptors are ligated to ends of a population of fragmented double-stranded DNA molecules to form a library of adaptor-ligated fragments, such that upon amplification of a fragment in the library of adaptor-ligated fragments, each end of the fragment has a distinct end. The library of adaptor-ligated fragments is diluted to form diluted, adaptor-ligated fragments. At least a portion of the diluted, adaptor-ligated fragments is amplified to form families from a single strand of an adaptor-ligated fragment. Family members are sequenced to obtain nucleotide sequence of a plurality of family members of an adaptor-ligated fragment. Nucleotide sequence of a member of a first family is aligned to a reference sequence. A difference between the member of the first family and the reference sequence is identified. The difference is identified as a potential rare or potential non-clonal mutation if it is found in a second family from an opposite strand of the single strand of the adaptor-ligated fragment.

According to one embodiment of the invention a method is provided for sequencing DNA. A double-stranded DNA population from a sample is randomly fragmented to form a library of fragments. Adaptors are ligated to ends of the fragments to form a library of adaptor-ligated fragments, such that upon amplification of a fragment in the library of adaptor-ligated fragments, each end of the fragment has a distinct end. The library of adaptor-ligated fragments is diluted to form diluted, adaptor-ligated fragments. At least a portion of the diluted, adaptor-ligated fragments is amplified to form families from a single strand of an adaptor-ligated fragment. Family members are sequenced to obtain nucleotide sequence of a plurality of family members of an adaptor-ligated fragment. Nucleotide sequence of a member of a first family is aligned to a reference sequence. A difference between the member of the first family and the reference sequence is identified. The difference is identified as a potential rare or potential non-clonal mutation if it is found in a second family from an opposite strand of the single strand of the adaptor-ligated fragment.

1. A method for sequencing DNA, comprising: randomly fragmenting a double-stranded DNA population from a sample to form a library of fragments; ligating adaptors to ends of the fragments to form a library of adaptor-ligated fragments, such that upon amplification of a fragment in the library of adaptor-ligated fragments, each end of the fragment has a distinct end; diluting the library of adaptor-ligated fragments to form diluted, adaptor-ligated fragments; amplifying at least a portion of the diluted, adaptor-ligated fragments to form families from a single strand of an adaptor-ligated fragment; sequencing family members to obtain nucleotide sequence of a plurality of family members of an adaptor-ligated fragment; aligning nucleotide sequence of a member of a first family to a reference sequence and identifying a difference between the member of the first family and the reference sequence; and identifying the difference as a potential rare or potential non-clonal mutation if it is found in a second family from an opposite strand of the single strand of the adaptor-ligated fragment. 7. The method of claim 1, wherein the difference is a two-base difference.

These and other embodiments which will be apparent to those of skill in the art upon reading the specification provide the art with methods for assessing mutations and mutation rates in an unbiased fashion.

BRIEF DESCRIPTION OF THE DRAWINGS

(FIG. 2A) Comparison of point mutation frequencies in nuclear (left graph) and mitochondrial (right graph) genome in age-matched normal colon epithelium (black circle) with different DNA mismatch repair genotypes (PMS2+/+ or PMS2−/−) or in age-matched normal kidney cortex (black square) without (no exposure) or with (aristolochic acid or smoking) carcinogen exposure. Red lines represent average. *P<0.05, t-test; P<0.001 and *P<0.0001 one-way ANOVA with Bonferroni multiple comparison post-test; n.s., not significant indicates P>0.05. (FIG. 2B) Stacked columns representing the substitution frequencies (y-axis) of each substitution out of the six possible substitution types (see legend). Cohort labels are indicated in (a) directly above each column. Number of substitutions (n) generating each mutational spectrum is indicated on the x-axis. n.d., not determined due to an insufficient number of mutations (n=7) for mutational spectrum analysis. *P=0.04, Fisher's exact test; P=2.58×10-8 and *P=1.51×10-16, Fisher's exact test with Bonferroni multiple comparison correction; ns, not significant indicate P>0.05. All statistical tests in FIG. 2 were two-tailed.

(FIG. 6A) Nuclear point mutation frequencies (y-axis) considering mutations observed in "Watson AND/OR Crick" (black circle) or "Watson AND Crick" families (black square) in normal tissues derived from brain frontal cortex (left side), kidney cortex (middle, shaded), or colon epithelium (right side). Specifically, "OR" mutations represent ≥90% mutation fraction in Watson family with a minimum of two Watson reads or ≥90% mutation fraction Crick family with a minimum of two Crick reads. Note that the "OR" mutations have only the Watson or Crick families represented in the data but not both. "AND" mutations represent ≥90% mutation fraction in Watson family with a minimum of two Watson reads and ≥90% mutation fraction Crick family with a minimum of two Crick reads. "AND" mutations are an internal subset of the "AND/OR" dataset, which is a modified version of the BotSeqS pipeline. Twenty-five individuals are organized by increasing age within each tissue. (FIG. 6B) Pie charts of the frequencies of each nuclear substitution out of the six possible substitution types (see legend) from (a) considering Watson AND/OR Crick (top pies) or Watson AND Crick (bottom pies) in each normal tissue type. The number of nuclear mutations generating mutational spectra for Watson AND/OR Crick was n=616 for brain, n=1,257 for kidney, n=2,542 for colon and for Watson AND Crick was n=33 for brain, n=74 for kidney, n=99 for colon.

(FIG. 9B) Principal component analysis (PCA) of mutational spectra from the cohorts indicated in (FIG. 9A). PCA performed and graphed using R software.

Figure 1:
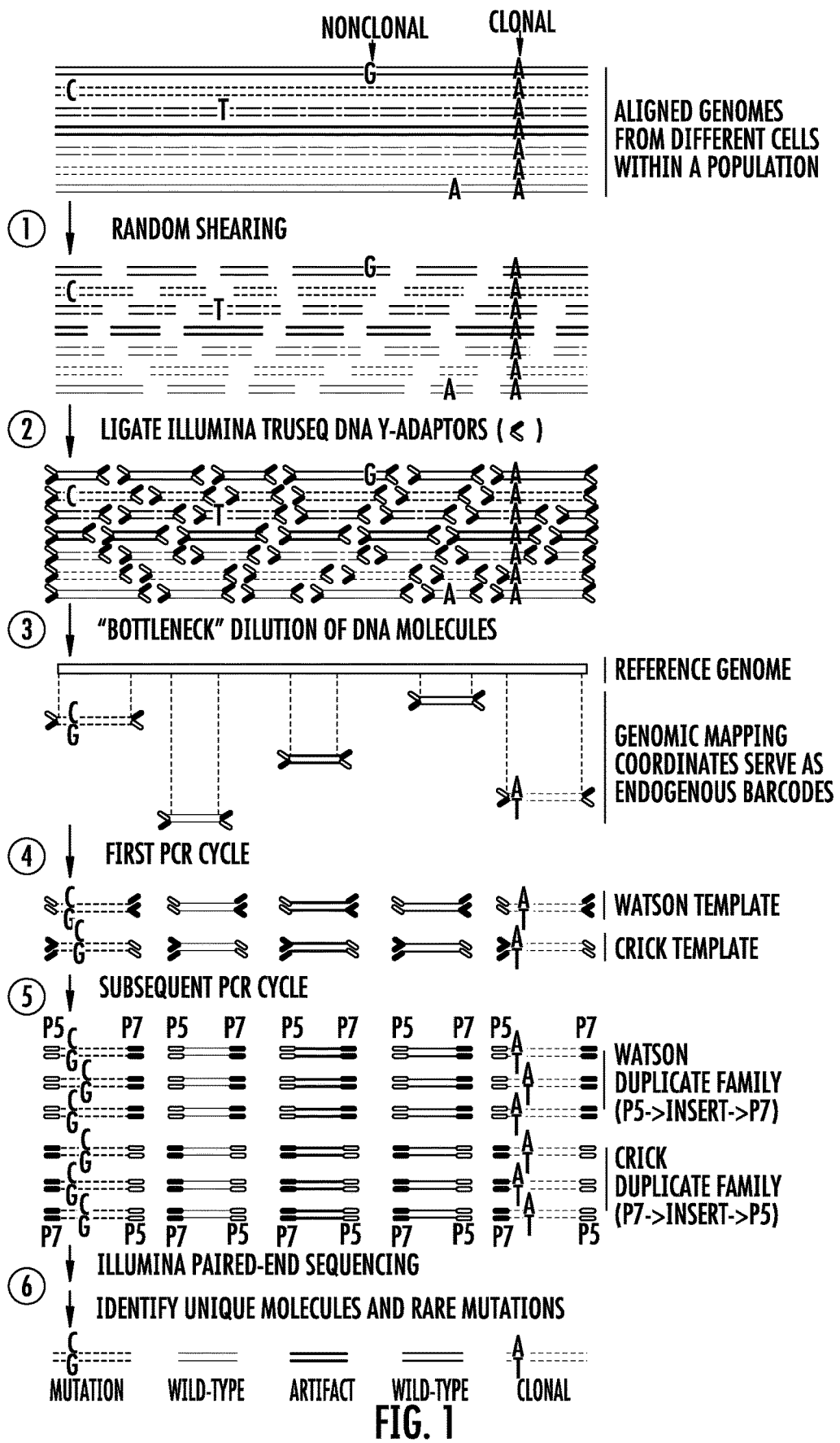
FIG. 1. Bottleneck sequencing methodology. Each color in the top panel represents double-stranded DNA from a genome of one cell within a population. Random, non-clonal point mutations (red) are private to individual cells. In contrast, clonal reference changes (A in black) are present in all genomes within the cell population. (1) Random shearing generates variably-sized DNA molecules. (2) Non-complementary single-stranded regions of the Illumina Y-adapters are represented as forked structures ligated to both ends of each DNA molecule. (3) Dilution decreases the number of DNA molecules (five are shown) from the original population in a random manner. Ends of the DNA molecules align uniquely to the reference genome. Mapping coordinates are used as unique molecule "barcodes" during data processing. (4) PCR primer (black arrowhead) anneals and primer extends (hashed lines) the Watson and Crick template of the original DNA molecule independently. Illumina P5 (grey) and P7 (black) containing adapters are specified here. (5) Watson and Crick templates generate two families of PCR duplicates. Orientation of P5 (grey) and P7 (black) containing adapters to the DNA molecule (insert) distinguishes the two families. P5 and P7 sequences dictate which end will be sequenced in Read 1 vs. Read 2, respectively, on the Illumina flow cell. In contrast to artifacts, real mutations (C: G mutation in red) will be present in both the Watson and Crick strands of the family members. (6) The BotSeqS pipeline identifies and quantifies the number of unique DNA molecules and point mutations (C: G in red) in the sequencing data by eliminating artifacts and clonal changes (A: T in black).

All supplementary tables are available on-line in the Proceedings of the National Academy of Sciences of the United States of America journal, Hoang et al., 113(35) PROC. NATL. ACAD. SCI. USA 9846-51 (2006) (doi: 10.1073/pnas.1607794113), and are incorporated herein by reference.

DETAILED DESCRIPTION OF THE INVENTION

The inventors have developed a method that can quantify rare somatic point mutations across the mitochondrial and nuclear genomes. One or more embodiments of the invention are referred to informally as BotSeqS, which is short for Bottleneck Sequencing System. Using molecular barcoding (exogenous or endogenous) and a simple dilution step immediately prior to library amplification, the method permits, for example, determining mutational burden based on age or tissue type of normal tissues. The method can also be used to demonstrate the effect of mutagens and environmental insults on mutation rate. The Bottleneck Sequencing System (BotSeqS) technology described in this work was designed to accurately detect rare point mutations in any molecularly-barcoded library in a completely unbiased fashion.

BotSeqS was developed to address questions that were not addressable by other methods including SafeSeqS (reference 10). It can be used with any molecular barcoding strategy, such as endogenous position-demarcated barcodes, described in the SafeSeqS paper, and exogenously added matched barcodes (references 10-13 and 15-18). BotSeqS measures very rare mutations, genome-wide in a completely unbiased fashion, whereas SafeSeqS measures relatively frequent but not clonal mutations (i.e., "sub-clonal") at pre-defined targeted loci. Conceptually, BotSeqS can be envisioned as achieving low coverage of randomly sampled genomic loci, whereas SafeSeqS works through ultra-high coverage of a targeted locus.

Low genomic coverage which can be seen as a feature of methods described here, permits rare mutations to constitute a major portion of the signal at that genomic position, contributing to the sensitivity of the method. The applications of the method are varied. It can be used to measure very rare somatic mutations. It can be used to assess somatic mosaicism, cell lineage development, theories on aging, environmental carcinogen exposure, and cancer risk assessment. Many of these applications are demonstrated below in the examples.

Various filters can be applied to the data that are generated with this sequencing method. One filter applied was for mtDNA only; Watson AND Crick duplicate families only, excluding templates that include high frequency mutations (i.e., homopolymers, >1 mutation per template) and excluding templates that map to repeatMasker. Another filter applied was for nuclear DNA only; Watson AND Crick duplicate families only, excluding templates that include high frequency mutations (i.e., homopolymers, >1 mutation per template) and excluding templates that map to repetitive DNA or structural variants. Another filter used was for mtDNA only, single-base substation only, average quality score of greater than or equal to 30, Read 1>=2 Watson duplicates with >=90% mutation fraction only, Read 2>=2 Crick duplicates with >=90% mutation fraction only, Exclude all variants called in WGS, Exclude all variants in dbSNP142, Exclude calls that map to repeatMasker, Exclude visual artifacts and high frequency mutations (i.e., homopolymers, cycle 6 and 7, >1 change per template>1 template per change). Yet another filter used was Nuclear DNA only, Single-base substitution only, Average quality score >=30, Read 1>=2 PCR duplicates with >=90% mutation fraction only, Read 2>=2 PCR duplicates with >=90% mutation fraction only, Exclude all variants called in WGS, Exclude all variants in dbSNP130 and dbSNP142, Exclude calls that map to repetitive DNA or structural variants, Exclude visual artifacts and high frequency mutations (i.e., homopolymers, cycle 6 and 7, >1 change per template).

Various databases were used to align and filter the data, including: dbSNP build 130, Database of Genome Variants, Segmental Duplications, Fragments of Interrupted Repeats, Simple Tandem Repeats, Repeat Masker, dbSNP build 142, updated Database of Genome Variants, updated Database of Genome Variants, updated Segmental Duplications, updated Fragments of Interrupted Repeats, updated Simple Tandem Repeats, updated Repeat Masker. The GRCh37/hg19 genome assembly from the USCS Human genome Browser was used.

Fragments of double stranded DNA can be made from longer chain polymers, using any technique known in the art, including but not limited to enzyme digestion, sonication, and shearing. Alternately, some sources of DNA are already fragmented at suitable sizes. Such sources include without limitation saliva, sputum, urine, plasma, and stool. If the source of DNA is already appropriately sized, then they need not be further fragmented. Desirably, the fragmentation process, whether endogenous or by human action, is random. The desirable size of fragments may depend on the length of sequencing reads. Fragments may be less than 2 kbp, less than 1500 bp, less than 1 kbp, less than 500 bp, less than 400 bp, less than 200 bp, or less than 100 bp. Fragments may desirably be greater than twice the read length, for example. Fragments may be at least 50 bp, at least 100 bp, at least 150 bp, at least 200 bp, at least 300 bp, at least 400 bp, at least 500 bp, for example.

Fragments will be ligated to adaptors. The goal is to have different adaptors on each end of a fragment. This can be a laborious process, that may involve much screening and processing to obtain fragments with two distinct adaptors on each end. One way to accomplish this goal is to use Y, U, or hairpin shaped adaptors which contain or can be processed to contain sequence non-complementary sequences on the Watson and Crick strands. If there is a non-complementary region in an adaptor, amplification of the adaptor-ligated fragment will generate double stranded fragments with different adaptor orientation on fragments derived from each strand, when amplified.

Dilution of libraries of adaptor-ligated fragments can be done using any level of dilution that is appropriate for the source. Less concentrated samples will require less dilution and more concentrated samples will require more dilution. Complexity of a sample will also factor into the desired degree of dilution. Any dilution series may be used as is convenient, such as two-fold dilutions, five-fold dilutions, ten-fold dilutions, etc. In one embodiment, a dilution level is chosen that will yield ~5-10 members of a family per adapter-ligated fragment. This is influenced by how many fragments are sequenced. For example, at one specific dilution, sequencing ~20 million clusters will yield 1-4 members, but sequencing 75 million clusters yield 5-10 (see FIG. 4). The more molecules that are sequenced, the higher the number of members that will be found per family. Upon sequencing family members derived from the diluted, adaptor-ligated fragments, one desirably obtains nucleotide sequence of 4-100 family members of an adaptor-ligated fragment.

Dilution may beneficially achieve a relatively low level of coverage of the genome. That is, the genome may be sampled rather than exhaustively and repetitively sequenced. In one embodiment, the dilution is sufficient so that less than 10 families from nuclear DNA comprise 20 or more overlapping nucleotides in the non-adaptor portion. In another embodiment, the dilution is sufficient so that less than 5 families from nuclear DNA comprise 20 or more overlapping nucleotides in the non-adaptor portion. In another embodiment, the dilution is sufficient so that less than 10 families comprise the potential rare or potential non-clonal difference detected between a test sequence and a reference sequence. In another embodiment, the dilution is sufficient so that less than 5 families comprise the potential rare or potential non-clonal difference detected between a test sequence and a reference sequence.

Dilution may accomplish three features. First, it will achieve lower coverage of representative loci to one or a few molecules to "uncover" rare mutations. Second, it will increase the chances that both strands of the initial molecules will be sequenced redundantly. Third, it will facilitate the random sampling of the genome with minimal amount of sequencing.

Amplification can be performed by any technique known in the art. Typically polymerase chain reaction will be used. Other techniques, whether linear or logarithmic may be used. Typically, primers will be used in the amplification that are complementary to adaptor sequences.

Sequencing can be accomplished by any known technique in the art. A next generation sequencing method may be used. The sequences of the fragments can be aligned to a reference sequence. They can be grouped into families on the basis of an endogenous or an exogenous barcode. An endogenous barcode typically comprises the N nucleotides that are adjacent to the adaptor. The value of N can be chosen as is convenient and provides sufficient diversity/complexity. Exogenous barcodes can be added in a separate ligation step, by amplification primers, or they can be part of the adaptors. Preferably the barcodes are random. Sequencing of from 2 to 1000 family members will be useful. In some situations, less than 100 family members can be sequenced. In some situations at least 4 family members will be sequenced. Sequencing of 4 to 10 family members may be desirable.

According to the method described here, one need not separate physically or analyze separately the nuclear and mitochondrial genomes. This permits one to compare rates in the two genomes in the same cells.

Exogenous barcoding may be used to identify individual fragments, samples, tissues, patients, etc. Although the examples below employed endogenous barcoding, this may be supplemented with or replaced by exogenous barcoding. If the barcode is to represent a particular fragment, the complexity of the barcode population should be greater than the complexity of the population of fragments to be barcoded. Barcodes can be added to a population of fragments using any technique known in the art, including by amplification or ligation, or as part of adaptor molecules that are added by ligation.

Differences that can be detected between a determined nucleotide sequence and a reference nucleotide sequence include without limitation mutations, such as point mutations, indels (insertions or deletions of 1-6 bases), and substitutions. If the same mutation is found in two different families, then a higher degree of certainty is attached to it, i.e., that it arose in the biological sample, rather than in the experimental processing. The two families have identical sequences deriving from the double stranded fragments, but they have a different orientation with respect to the adaptor sequences. To achieve a higher degree of certainty, one can require that at least two members of each of two families have the sequence difference. To achieve a higher degree of certainty, one can require that 90% or more of the members of a family have the sequence difference.

As a means of filtering out germline or clonal mutations, libraries of fragments that have not been amplified and which are from the same sample can be sequenced. Germline and clonal mutations will be evident from inspection because of their repeated occurrences.

BotSeqS is a simply-implemented NGS-based approach that can accurately measure rare point mutations in an unbiased, genome-wide manner. Using BotSeqS, we were able to achieve several important goals: (i) define estimates of rare mutation frequencies across the whole genome; (ii) simultaneously evaluate rare mutations in both the nuclear and mitochondrial genomes of the same population of cells; (iii) compare rare mutation frequencies among various normal tissues of individuals of different age, DNA repair capacity, or exposure histories; and (iv) identify the spectra of rare mutations in normal tissues, allowing their comparison to those of clonal mutations in cancers.

Our data show that mutations increase with age, a result that is broadly consistent with the literature[2, 3]. The rate of increase of mutations is not as great in brain as it is in colon or kidney, presumably because the colon and kidney are both self-renewing tissues throughout adult life while the brain is not. On the other hand, the fact that the mutation frequency increased at all after childhood was surprising, given that the major cell types in pre-frontal cortex are generally thought to be post-mitotic[28]. There are several potential explanations for this increase. A small number of cells that are replicating more actively than neurons or glia could be responsible for the increase. Such cells could include microglia or infiltrating lymphocytes or other inflammatory cells. Alternatively, these mutations could represent the results of spontaneous DNA damage independent of DNA replication. A recent single-cell sequencing study of human neurons suggested that spontaneous damage occurs during transcription[29].

However, in contrast to single-cell sequencing, BotSeqS measures mutations that are found on both strands. Thus for the explanation of spontaneous DNA damage to be plausible, the mutations identified by BotSeqS would have to have been subject to DNA repair. Consistent with this possibility, DNA repair processes are known to be active in post-mitotic neurons and glia[30].

A third possibility is that these mutations are artifacts of the procedure we used to detect them. It is fascinating that this formal possibility is essentially impossible to exclude because the mutations we detected are likely found in only one cell of the tissue studied, and the DNA from that cell is no longer available for subsequent evaluation. Additionally, there is no other technique available to observe such mutations with the sensitivity achieved here. Our sensitivity is currently limited only by the amount of sequencing devoted to the project. We can easily detect mutations occurring at $6\times10^{-8}$ per bp using a small fraction of a HISEQ™ 2500 flow cell. We estimate that mutations could be detected at $<10^{-9}$ per bp using an entire flow cell. The only other method that approaches this sensitivity has been described by Loeb and colleagues[12, 31], but this is applicable only to pre-defined regions (~0.001%) of the genome. In the absence of direct confirmation, we are forced to use correlations and other approaches to support the accuracy of the technology described herein. These correlations include the following, as detailed in Supplementary Table 9 (available online in the Proceedings of the National Academy of Sciences of the United States of America journal, Hoang et al. 113(35) PROC. NATL. ACAD. SCI. USA 9846-51 (2006) (doi: 10.1073/pnas.1607794113): similar mutation frequencies and spectra identified in different DNA aliquots of the same samples; similar mutation frequencies and spectra identified in the same tissues of different individuals of similar age; expected increases in mutation frequencies with age; tissue-specific differences in age-dependent increases in mutation frequencies; higher mutation frequencies in normal tissues deficient in mismatch repair or exposed to environmental mutagens; and mutation spectra in normal tissues consistent with those previously observed in cancers from the same tissues. Other in silico and experimental approaches used to evaluate the accuracy of BotSeqS are described in the Example 1.

We also were able to compare mutation frequencies in the mitochondrial and nuclear genomes of the same tissues. In normal individuals in the absence of exposure to mutagens, the mutation frequency was much higher in the mitochondria than in the nuclear genome (median ratio of 26.2). This is consistent with the relatively poor efficiency of DNA repair in the mitochondria compared to the nuclear genome[32]. Equally important, however, is that the ratio of mitochondrial to nuclear mutation frequencies was vastly lower (median of 1.3) in the normal kidneys of individuals exposed to either cigarette smoke or AA. This finding is not consistent with the known, less efficient repair of DNA in mitochondria. Moreover, there was a shift towards the AA mutational signature, A:T to T:A transversions, in the nuclear DNA of normal kidneys in individuals exposed to AA, but virtually none in the mtDNA. One possibility is that the higher mutation prevalence in the mtDNA could be masking the effect of environmental mutagens on the mitochondrial genome compared to its effect on the nuclear genome. Another possibility is that there are unexpected and pronounced differences in the ways through which these mutagens cause DNA damage in these two organelles.

Another novel point of our study is the finding that mutation spectra differed among normal tissues, even in the absence of exposures to known mutagens. Whether such differences reflect varying exposures to as yet unidentified commonly encountered mutagens, or tissue-specific repair processes, is not known. In some cases, the rare mutation spectra in normal tissues were found to be similar to the clonal mutations found in cancers. Though varying mutation spectra in cancers has often been attributed to cancer-specific processes, our data suggest that at least a subset of these mutations actually reflect tissue-specific processes. This concept is consistent with the idea that a substantial fraction of the mutations found in cancers occur in normal stem cells[33, 34] We envision that the straightforward approach described here, which can easily measure very rare mutations in any tissue or cell type of interest, will be applicable to questions of broad biomedical interest.

young adult body at ~20-40 years, and old, maintained adult body at >90 years. For colon, one tissue from the young child age group (SIN230) was later determined to be duodenum, leaving only two individuals representing the young child age group for colon epithelium. For normal kidney, criteria for kidney acquisition were an age-matched and non-smoking control group for the kidneys of smokers and aristolochic acid-exposed samples. All normal kidney controls were Caucasian and therefore less likely to originate from a high risk AA-exposed population (e.g. Asia). From the same kidney tissue source, three aliquots of flash frozen, post-mortem normal kidney from a five month old individual were available as technical replicates and to further test an age-trend for non-carcinogen exposed normal kidneys.

TABLE 1

Summary of rare mutation frequencies in normal human tissues

| Genome | Normal Tissue | Number of Individuals | Young Child Mutation Frequency ($\times 10^{-7}$ mutations/bp) | Young Adult Mutation Frequency ($\times 10^{-7}$ mutations/bp) | Old Adult Mutation Frequency ($\times 10^{-7}$ mutations/bp) | Average Lifespan (years) | Lifespan Fold-Difference |
|---|---|---|---|---|---|---|---|
| mtDNA | Brain | 9 | 18 ± 7 | 43 ± 6 | 131 ± 18 | 89.5 | 7.3 |
| | Kidney | 5 | 15 | nd | 277 ± 64 | 63.8 | 18.5 |
| | Colon | 11 | 12 ± 17 | 112 ± 43 | 365 ± 103 | 90.8 | 30.4 |
| Nuclear | Brain | 9 | 1.1 ± 0.3 | 2.2 ± 1.1 | 6.3 ± 2.3 | 89.5 | 5.7 |
| | Kidney | 5 | 1.2 | nd | 7.8 ± 1.5 | 63.8 | 6.5 |
| | Colon | 11 | 1.8 ± 0.5 | 5.5 ± 1.6 | 11 ± 1.5 | 90.8 | 6.1 | nd, not determined

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1—Methods

Human Tissue Samples.

Normal, non-diseased tissues for this study were acquired from five different sources (Supplementary Table 1). For COL229 to COL237 and SIN230, colon or duodenum was obtained from consented patients at the Johns Hopkins Hospital with the approval of its Institutional Review Board. For COL373 to COL375 and BRA01 to BRA09, flash frozen, post-mortem colon and brain was requested from the NIH NeuroBioBank (www.neurobiobank.nih.gov), with the request being approved and fulfilled by University of Maryland Brain and Tissue Bank (Baltimore, Maryland) and University of Miami Brain Endowment Bank (Miami, Florida). For KID034 to KID038, flash frozen, post-mortem kidney cortex blocks (200 mg) were purchased from Windber Research Institute (Windber, Pennsylvania). COL238 and COL239 were previously reported 22, 35, 36. SA_117, SA_118, SA_119, AA_105, AA_124, and AA_126 were from Drs. C-H Chen and Y-S Pu of the Department of Urology, National Taiwan University Hospital and College of Medicine, Taipei, Taiwan as previously reported24. The initial rationale for the sample size for colon and brain was to acquire at least three individuals in each age group in order to understand the average trend of somatic mutational patterns for each age group. Age groups for colon and brain were selected based on human body growth and maintenance: early body development at <10 years, fully grown Preparation of Illumina Y-Adapter-Ligated Molecules.

Genomic DNA (34 ng to 1 μg) in 55 μL TE buffer was fragmented using BIORUPTOR® (Diagenode) at high intensity for 15 s on and 90 s off, using 7 cycles at 3° C. After random fragmentation, Illumina Y-adapters were ligated to the DNA fragments using TRUSEQ™ DNA PCR-Free kit (Illumina) according to a standard low DNA input Illumina protocol with selection for 350 bp insert sizes. This resulted in adapter-ligated molecules in a total volume of 20 μL.

Dilution of Y-Adapter-Ligated Molecules.

Five ten-fold serial dilutions were performed in 96-well PCR plates starting with 2 μL of adapter-ligated molecules (prior to PCR) in 18 μL of dilution buffer (TE containing 1 ng/0_, pBlueScript). Samples were mixed by gently pipetting with a multichannel pipette. Two μL of each sample was then transferred into 18 μL of fresh dilution buffer using a multichannel pipette. The mixing and transferring was repeated for a total of five serial dilutions. Only 2 μL of each dilution (1/10 total volume) was used as template for each PCR. A 103-fold dilution was accomplished as follows: (i) use of 2 μL of the total 20 μL of adapter-ligated molecules (10-fold dilution); (ii) mixing 2 μL of adapter-ligated molecules with dilution buffer in a total volume of 20 μL (10-fold dilution); and (iii) use of 2 μL of diluted adapter-ligated molecules from the total 20 μL volume in the PCR reaction (10-fold dilution, see below). The five serial dilutions resulted in final dilution factors of 103, 104, 105, 106, and 107.

PCR Amplification of Diluted Y-Adapter-Ligated Molecules.

Custom HPLC-purified PCR primers (IDT), TS-PCR Oligo1 (5'-AATGATACGGCGACCACCGAG*A; SEQ ID NO: 1) and TS-PCR Oligo2 (5'-CAAGCAGAAGACGGCATACGA*G; SEQ ID NO: 2), were designed with one phosphorothioated bond (*) at the 3' end. PCR was performed in 50 μL total volume with 0.5 μM TS-PCR Oligo1, 0.5 µM TS-PCR Oligo2, Q5 2× HotStart High-Fidelity Master Mix (NEB) at 1× final concentration, and 2 µL of diluted adapter-ligated molecules as template. PCR was performed in Thermo HyBaid PCR Express HBPX Thermal Cycler. The following PCR program was used: 1) 98° C. for 30 s 2) 98° C. for 10 s, 69° C. for 30 s, 72° C. for 30 s for 18 cycles, and 3) 72° for 2 min. PCR reactions were purified with AMPURE® XP (Agilent) at 1.0× bead-to-sample ratio according to the manufacturer's protocol.

MISEQ™ run and analysis. A subset of amplified BotSeqS sequencing libraries was evaluated on an Illumina MISEQ™ instrument (~5 M clusters passed filter per library) to empirically deduce the optimal dilution. The "optimal dilution" was determined to result in 5 to 10 PCR duplicates per molecule when scaled to ½ lane of a HISEQ™ instrument (~70 M clusters passed filter per library in Rapid Run mode). For example, for an input of 500 ng gDNA into the TRUSEQ™ PCR-free library prep (selecting for 350 bp insert size), amplified libraries from the 104-, 105-, 106-fold dilutions were sequenced at 2×50 bp depth on MISEQ™. Three different well-barcoded samples (which were also molecularly barcoded) were multiplexed in one MISEQ™ lane to test three dilutions of each sample. The .bam output files were uploaded into Galaxy, and Picard's Estimate Library Complexity Tool (Galaxy Tool Version 1.56.0) was executed using the default parameters. Optimal dilutions showed distributions ranging from one to four members per family with singletons comprising ~60-80% of total counts. In general, with an input of 500 ng of gDNA into the TRUSEQ™ PCR-free library prep, the 105-fold dilution yielded ~10 members per family on a subsequent HISEQ™ used for BotSeqS. From our sequencing data, we estimate the average number of high quality clusters required to identify one rare mutation in colonic tissues was (1) 30 M in a normal child, (2) 12 M in a normal young adult, and (3) 5.8 M in a normal old adult.

Whole-Genome Sequencing.

Thirty-two whole-genome sequencing (WGS) libraries were generated from the 34 individuals in this study. In the remaining two individuals without WGS, COL238 and COL239, Sanger sequence was performed to exclude clonal variants in the BotSeqS data. Of the final 20 µL of adapter-ligated molecules used to prepare BotSeqS libraries (prior to dilution), 10 µL was used to amplify a library for whole-genome sequencing using TRUSEQ™ PCR Primer Cocktail (Illumina) and TRUSEQ™ PCR Master Mix (Illumina) according to TRUSEQ™ PCR protocol. PCR reactions were purified with AMPURE® XP (Agilent) at 1.0× bead-to-sample ratio according to the manufacturer's instructions. The libraries were PE sequenced 2×100 bp on Illumina HISEQ™ at >30× coverage.

Spike-in Sensitivity Experiment.

Two DNA mixtures were prepared from the DNA of normal spleen samples PEN93 and PEN95. Whole genome sequence data was available from these two samples37 and SNPs in PEN93 that were not present in PEN95 could be identified. Both mixtures contained the same amount of PEN95 DNA, but the low spike-in mix contained only 10% of the PEN93 DNA contained in the high spike-in mix. BotSeqS libraries from these samples were first analyzed using the normal BotSeqS pipeline to minimize clonal and germline mutations. Indeed only a total of two mutations were detected among the two libraries; these two mutations likely represented rare mutations in the PEN95 sample, and suggest a mutation frequency of ~8×10-7 mutation/bp. Next, the data were processed through the BotSeqS pipeline without filtering out mutations that were present in dbSNP (build 130 and 142). Seven PEN93-specific SNPs in the low spike-in and 89 PEN93-specific SNPs in the high spike-in mixtures were identified. After normalizing for the number of sequenced bases, the "mutation frequency" (number of PEN93-specific SNPs/bp) was 2.71×10-6 for the low spike-in and 2.01×10-5 for the high spike-in samples. The difference between the low spike-in and the high spike-in was 7.4-fold, within the range expected from the 10-fold dilution given the relatively low number of mutations identified in the low spike-in sample.

Characterization of BotSeqS Specificity.

As one measure of specificity, we identified rare mutations as usual except that we used mutations that were present in only one strand rather than in both. Specifically, mutations were present in ≥90% of the Watson family members and the reference sequence was present in ≥90% of the Crick family members, or vice versa, but satisfied our other criteria for being "rare". We then created false Watson and Crick pairings, where the Watson strand had overlapping but different coordinates than the Crick strand, and vice versa, to determine if they contained the same mutation by chance. BotSeqS works by having low coverage throughout the genome, generated through the bottleneck dilution step, and precluded this analysis in the nuclear DNA. Instead, we used mtDNA because of the multiple copies of mtDNA per cell. The coverage of mtDNA with BotSeqS is much higher than that of nuclear DNA and facilitated the identification of overlapping molecules. We processed 30 BotSeqS control libraries this way and identified a total of 146 mtDNA mutations present in one strand only. Using this dataset, we then searched within each sample for overlapping molecules and identified 27 examples. None of the 27 false Watson and Crick pairs shared the same artifactual mutation.

Non-random shearing could produce another type of artifact, falsely suggesting that the Watson and Crick strands of a family were actually derived from two different molecules that coincidentally had the same genomic coordinate. To test for such artifacts, we identified Watson and Crick family pairs that contained the variant in the Watson strand and the reference sequence in the Crick strand, or vice versa, but this time included heterozygous germline variants rather than just the rare variants, and in nuclear DNA rather than in mtDNA. There are many more heterozygous variants in nuclear DNA than in mtDNA because the mtDNA is derived only from the oocyte. The discordances of interest could arise as a result of mispairing of a Watson strand with a Crick strand derived from a different template molecule—i.e., non-random shearing. Alternatively, discordances could result from an amplification error in one of the two strands during an early PCR cycle. Using our WGS data, we first identified 8,535,891 nuclear heterozygous variants observed among the 30 DNA samples used for the control BotSeqS libraries (median of 268,180 variants per library with range 121,851 to 529,922, with the same common variants present in many libraries). From the 8,535,891 nuclear heterozygous variants, we identified a total of 3,960,818 families (median of 123,134 families per library with range 65,832 to 222,135) for which both strands could be evaluated. Of these, 3,960,807 families had the concordant sequence at the variant position in both strands; only 11 heterozygous variants were discordant (i.e., the variant was present in ≥90% of the Watson family members and the reference sequence was present in ≥90% of the Crick family members, or vice versa). The rate of discordant germline heterozygous variants was thus $2.78 \times 10^{-6}$ (11 out of 3,960,818) per bp. This rate is compatible with the known error rate of high fidelity DNA polymerases and could easily represent an amplification error that occurred in one of the two strands during the first PCR cycle, so represents an overestimate of shearing artifacts. Furthermore, it is important to note that BotSeqS eliminates such amplification errors by requiring mutations to be observed on both strands. Because BotSeqS requires mutations to be observed on both strands, the actual false positive rate can be estimated to be ~(⅓)(2.78×10⁻⁶)(2.78× 10⁻⁶)=2.58×10⁻¹².

Generation of BotSeqS Change and Molecule Tables.

Sequence alignments and variant calling were performed with the Illumina secondary analysis package (CASAVA 1.8) using ELANDv2 matching to the GRCh37/hg19 human reference genome. High-quality reads were selected for further analysis only if they satisfied all of the following criteria: (i) passed chastity filter, (ii) read mapped in a proper pair, (iii) ≤5 mismatches to reference sequence, and (iv) perfect identity to reference sequence within the first and last five bases of each read. Sequencing reads were grouped into families based on identical paired-end endogenous barcodes. The members of a family were further subdivided into the two possible sequencing orientations to determine the number of Watson and Crick-derived family members. Watson and Crick families had identical genomic coordinates with each end sequenced in opposite reads. Quality scores of identical changes within a family were calculated as the average among the family members. The output for each BotSeqS library was two annotated tables of changes and template molecules (i.e., families).

Selection of High Quality Changes and Molecules.

Custom algorithms were written in Microsoft SQL Server Management Studio to query the changes and molecules tables for each BotSeqS library. Selection criteria are detailed in Supplementary Tables 2-6 (available online in the Proceedings of the National Academy of Sciences of the United States of America journal, Hoang et al . . . 113(35) PROC. NATL. ACAD. SCI. USA 9846-51 (2006) (doi: 10.1073/pnas. 1607794113). In general, selection was based on quality, clonality, and mappability of single base pair substitutions. For example, it is known that one of the major sources of errors facing all short read alignment and variant callers are artifacts that arise when variants map to repetitive regions in the genome, including low complexity regions and copy number variants38. The BotSeqS pipeline eliminates this universal error in a downstream step by filtering out the genomic noise from repetitive DNA and structural variants (detailed in Supplemental Table 6, available online in the Proceedings of the National Academy of Sciences of the United States of America journal, Hoang et al., 113(35) PROC. NATL. ACAD. SCI. USA 9846-51 (2006) (doi: 10.1073/pnas.1607794113). Indels were excluded because they are prone to alignment artifacts and are ~10 times less frequent than spontaneous point mutations. High quality single-base substitutions were defined as those with average quality scores (within the family) of ≥Q30 and with ≥2 reads and ≥90% mutation fraction in both the Watson and Crick strands. Variants were considered to be clonal if the variant position was present in the WGS data from that sample or observed in >1 template molecules (i.e., both strands of more than one UID). We also excluded any positions present in dbSNP130 or dbSNP142. We noticed that the dbSNP filtering drastically minimized recurrent sequencing or mapping artifacts and highly mutable regions. For example, homopolymer tracts (>8 bp) are mutation hotspots that flood the mutation list. We observed that nearly all were filtered out with dbSNP142. Finally, families that harbored >1 mutation were excluded as possible mapping artifacts.

Calculation of Mutation Frequency.

Mutation frequencies were determined for each BotSeqS library (see Supplementary Table 9, available online in the Proceedings of the National Academy of Sciences of the United States of America journal, Hoang et al., 113(35) PROC. NATL. ACAD. SCI. USA 9846-51 (2006) (doi: 10.1073/pnas.1607794113) by dividing the total number of rare mutations by the total bp sequenced. The total bp sequenced was defined by number of families×2×read length of each family. The average length of the libraries was ~500 bp such that the 100 bp paired-end reads were unlikely to overlap. Only templates with perfect identity to the reference sequence in the first and last 5 bp of every read were considered. We further trimmed the reads by excluding cycle 6 and 7 to ensure quality. Therefore, the actual read length was 88 bases (100−7−5=88). For the samples from which technical replicate BotSeqS libraries were generated, the average mutation frequency of the technical replicates was considered the mutation frequency for the sample.

Validation of Somatic Mutations.

All rare mutations from the nuclear and mtDNA genome passed visual inspection of the sequencing reads. For rare nuclear mutations, Sanger sequencing was performed on a representative set (514 out of 876 mutations). Of these, 514 of 514 (100%) were confirmed to be invisible by Sanger sequencing (excluding the COL238 and COL239 samples that did not have a matched WGS). This demonstrated that these mutations were neither present in the germline nor present in a highly clonal fashion. Mutations confirmed to be absent upon Sanger sequencing are indicated in Supplementary Table 8 (available online in the Proceedings of the National Academy of Sciences of the United States of America journal, Hoang et al., 113(35) PROC. NATL. ACAD. SCI. USA 9846-51 (2006) (doi: 10.1073/pnas. 1607794113).

Comparison to Cancer Genomes.

Nineteen MAF files representing nuclear somatic mutations from 19 TCGA tumor types were downloaded from the synapse website (TCGA dataset #!Synapse:syn1729383). From the TCGA data, only single-base substitutions were considered and somatic mutations from ultra-mutated tumors were excluded. Mitochondrial DNA somatic mutations from colorectal and renal tumors were derived from supplementary file 2 of a previous report[26].

Statistics.

For study design, no prior power analysis or randomization was performed because the variance was initially unknown. The goal of the study was to find major, biologically meaningful differences between the cohorts. To find major differences, sample sizes can be small. Even with the small sample size, however, no violations of the assumptions of the tests were detected, including violations about the homogeneity of variances. T-test and ANOVA analyses were performed using GRAPHPAD PRISM™ 5.0f. Fisher's exact test was performed using R version 3.2.2. Principal component analysis was performed in R. All analyzed samples were reported in the manuscript.

Example 2

Principles Underlying BotSeqS.

The principal feature of BotSeqS is the dilution of any type of a sequencing library prior to PCR amplification. This dilution creates a bottleneck and permits an efficient, random sampling of double-stranded template molecules with a minimal amount of sequencing. Rare mutations, which would normally be masked by an abundance of wild-type sequences in conventional libraries, account for much more of the signal at the corresponding genomic position in a bottlenecked library. Dilution also increases the likelihood that both the "Watson" and "Crick" strands of a DNA molecule will be sequenced redundantly, a feature critical for the high accuracy of BotSeqS and the relatively small amount of sequencing required to implement it. The presence of the same rare mutation on both strands can substantially decrease artifacts and increase specificity[12]. Finally, the random nature of dilution allows DNA molecules from both nuclear and mitochondrial genomes to be assessed from one library.

Example 3

Generation of BotSeqS Libraries.

A standard Illumina TRUSEQ™ PCR-Free kit was used to generate 44 BotSeqS libraries from the normal tissues of 34 individuals (Supplementary Table 1, available online in the Proceedings of the National Academy of Sciences of the United States of America journal, Hoang et al., 113(35) PROC. NATL. ACAD. SCI. USA 9846-51 (2006) (doi: 10.1073/pnas. 1607794113). This included nine individuals with one or two technical replicates. In addition, 10 of our 12 cohorts had more than one biological replicate, each containing two to six individuals.

Figure 4:
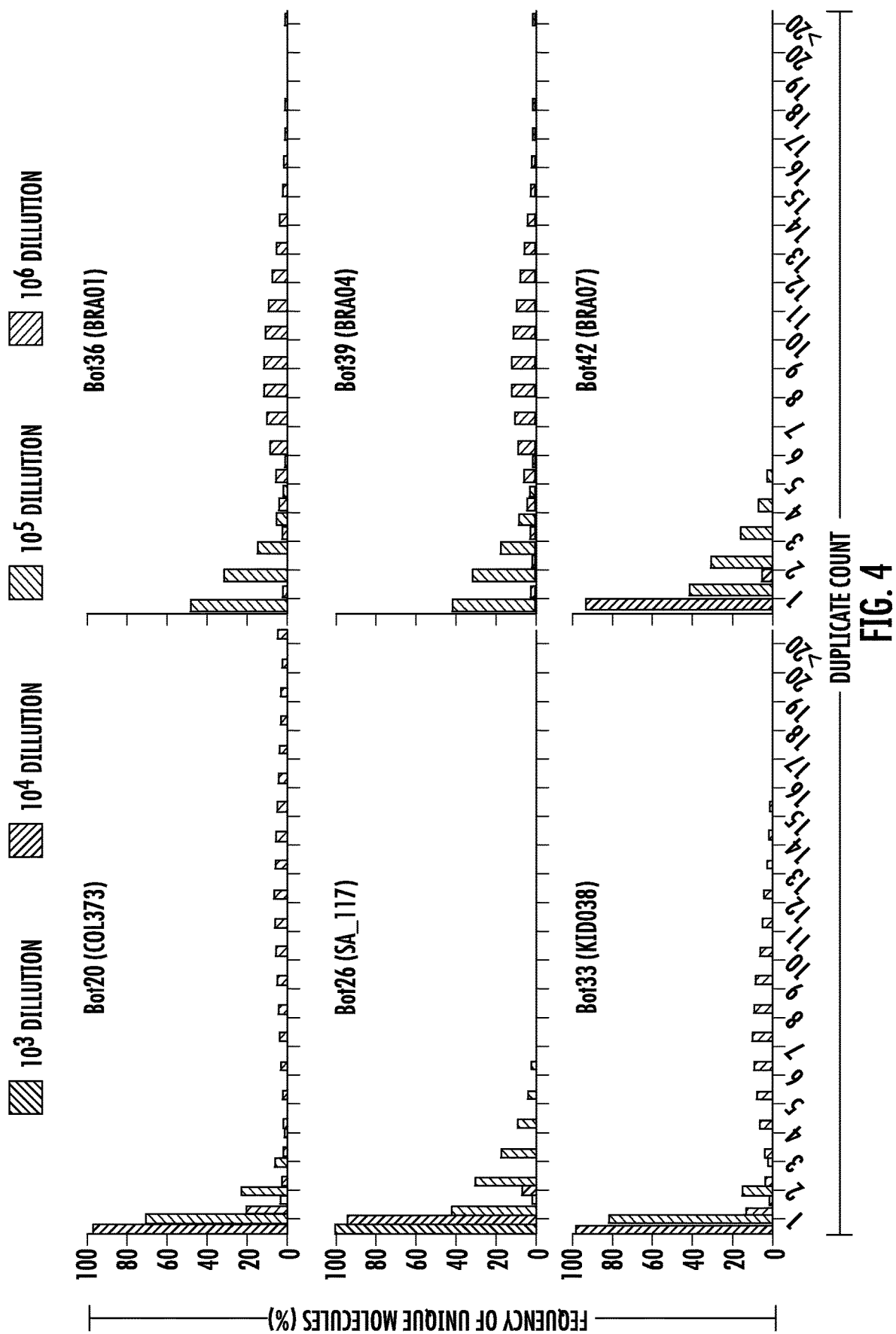
FIG. 4. Assessment of duplicate counts with MISEQ™ prerun. Histograms showing the distribution of family members (PCR duplicates from individual template molecules, shown on the x-axis). Either two or three serial dilutions ($10^3$, $10^4$, $10^5$, or $10^6$) were evaluated on the MISEQ™ for six samples (COL373, SA_117, KID038, BRA01, BRA04, BRA07) to generate ~5 M properly paired reads per library. Family member counts were determined here using Picard's Estimate Library Complexity program. Libraries generated from the $10^5$ dilution (blue) were subsequently used for the final HISEQ™ run reported in this study. Note that the HISEQ™ distribution is expected to shift to the right compared to the MISEQ™ distribution due to the increase of clusters sequenced per library (~5 M clusters scaled to ~70 M clusters). For example, the BotSeqS libraries from the $10^6$ dilution (red) were not used because the members per family would be too high on a HISEQ™ run, limiting the number of different families that could be evaluated with a given amount of sequencing.

The preparation of BotSeqS libraries starts with the random shearing of genomic DNA (FIG. 1). This fragments the genomes into variably-sized DNA molecules, each possessing unique end coordinates called endogenous barcodes[10]. Following ligation of standard sequencing adapters to the DNA molecules, the library is diluted to reduce the number of molecules in the population. To identify the correct dilution factor, a ten-fold dilution series was assessed on a MISEQ™ instrument (FIG. 4). After dilution, PCR amplification of the library generates multiple copies (duplicates) of each DNA molecule. The endogenous barcodes enables the grouping of sequencing reads into families, also known as UIDs, for unique identifiers[10]; each family represents the PCR-derived progeny of a single-stranded template and each member of a family represents the sequence from a single cluster on the Illumina instrument. In the following, we consider the Watson strand to be the sequence derived from the first read of the sequencing instrument (Illumina adapter P5) and the Crick strand to be the sequence derived from the second read (Illumina adapter P7) of each member of the family (FIG. 1). To be considered a potential mutation, BotSeqS required that the identical sequence change be observed in >90% of the Watson and in >90% of the Crick family members and that each family be composed of at least two members. BotSeqS libraries were analyzed using an Illumina HISEQ™ 2500 instrument on rapid run mode with paired-end reads of 100 bases each. A median of 70 million (M) clusters per library passed the standard Illumina quality filters (range 37 to 188 M clusters per library; Supplementary Table 1, available online in the Proceedings of the National Academy of Sciences of the United States of America journal, Hoang et al., 113(35) PROC. NATL. ACAD. SCI. USA 9846-51 (2006) (doi: 10.1073/pnas. 1607794113).

Example 4

BotSeqS Data Processing Pipeline.

Figure 5:
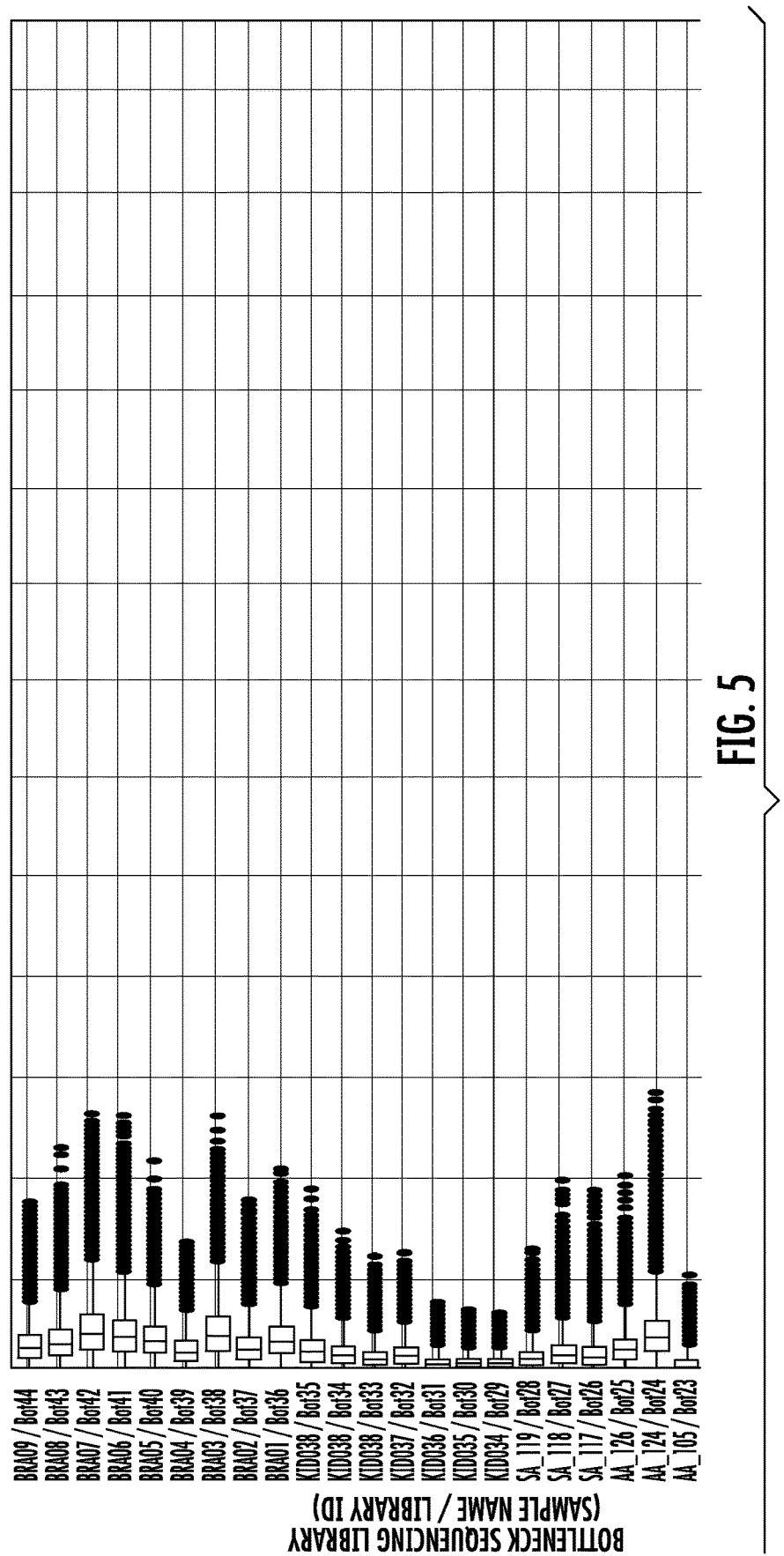
FIG. 5. Family member counts of 44 BotSeqS libraries reported in this study. Horizontal box and whisker plots for 44 BotSeqS libraries (y-axis) and number of members per family (duplicate count, x-axis). White boxes represent the first to third quartile range with the hash mark indicating the median. Whiskers represent 1.5*IQR (interquartile range) and data points outside the whiskers are shown as outliers. An average of 3.97 M (range 0.38 to 10.91 M) unfiltered families per library were assessed. Families were identified through the BotSeqS pipeline using the genomic mapping coordinates as unique molecule identifiers. Names in blue indicate technical replicate samples. Note that Bot01-Bot06 and Bot23-28 were performed on the same samples with a 100-fold difference in dilution (see Supplementary Table 1; available online in the Proceedings of the National Academy of Sciences of the United States of America journal, Hoang et al., 113(35) PROC. NATL. ACAD. SCI. USA 9846-51 (2006) (doi: 10.1073/pnas. 1607794113)).
Figure 5:
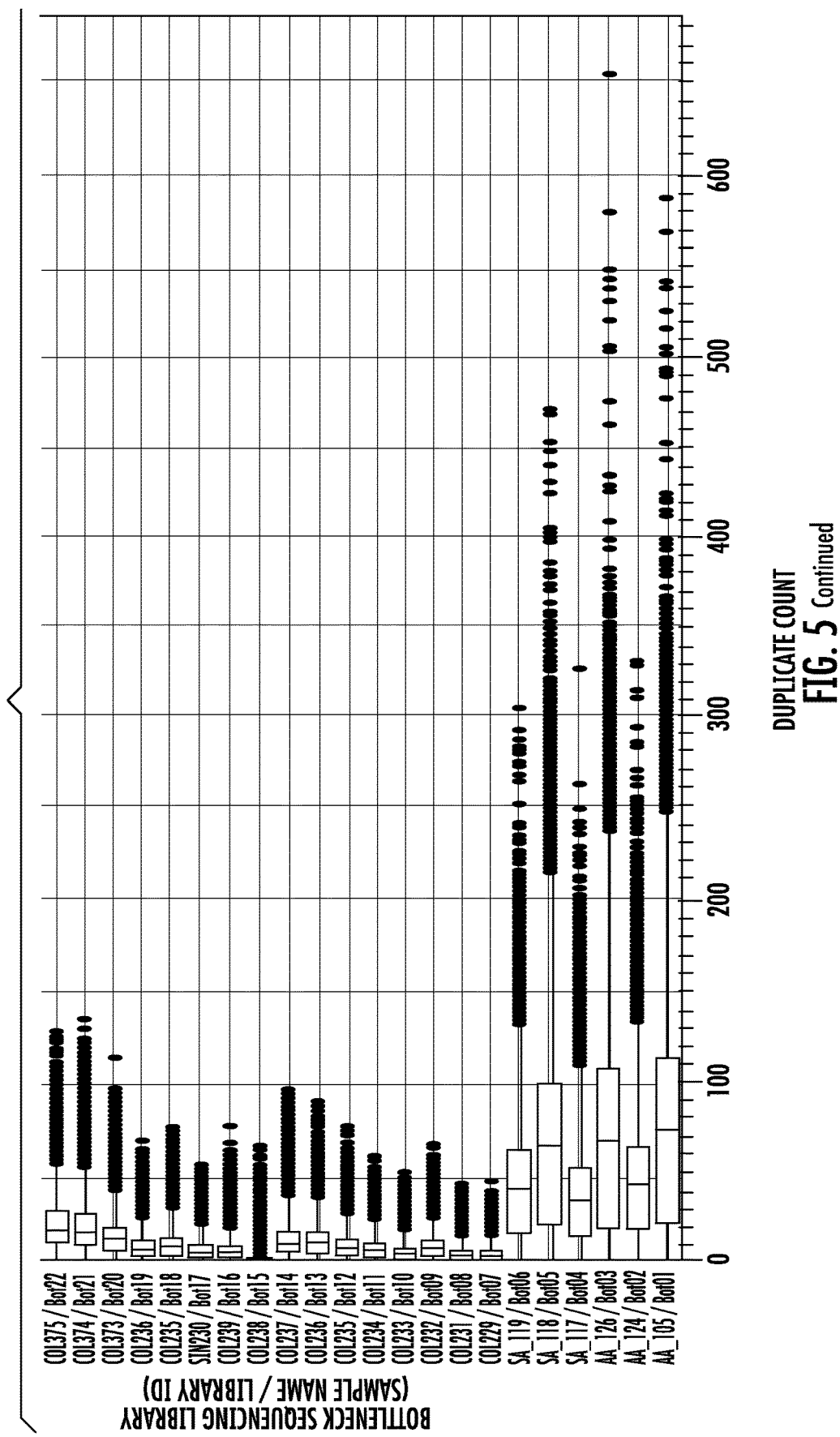

The goal of the BotSeqS pipeline was to accurately identify rare, somatic point mutations and to calculate the frequency of these mutations in the sample. To process the data for this purpose, raw sequencing data were input into Illumina's secondary analysis package (CASAVA 1.8) with ELANDv2 mapping to GRCh37/hg19 human reference genome. The BotSeqS pipeline begins by selecting high quality reads for analysis (see Example 1). The data are then organized into two tables for each BotSeqS library: (i) a "change" table listing all differences from the reference sequence and (ii) a unique molecule table listing all families. Importantly, each table contains strand information; almost half (median 45%, range 8% to 62%) of the unique molecules from each BotSeqS library had both the Watson and Crick strands represented in the dataset, ensuring specificity in the subsequent mutation analysis. Moreover, most BotSeqS libraries (37 of 44) had a median number of family members between 5 and 20 (FIG. 5), further demonstrating that the libraries underwent successful bottlenecking.

Figure 6A:
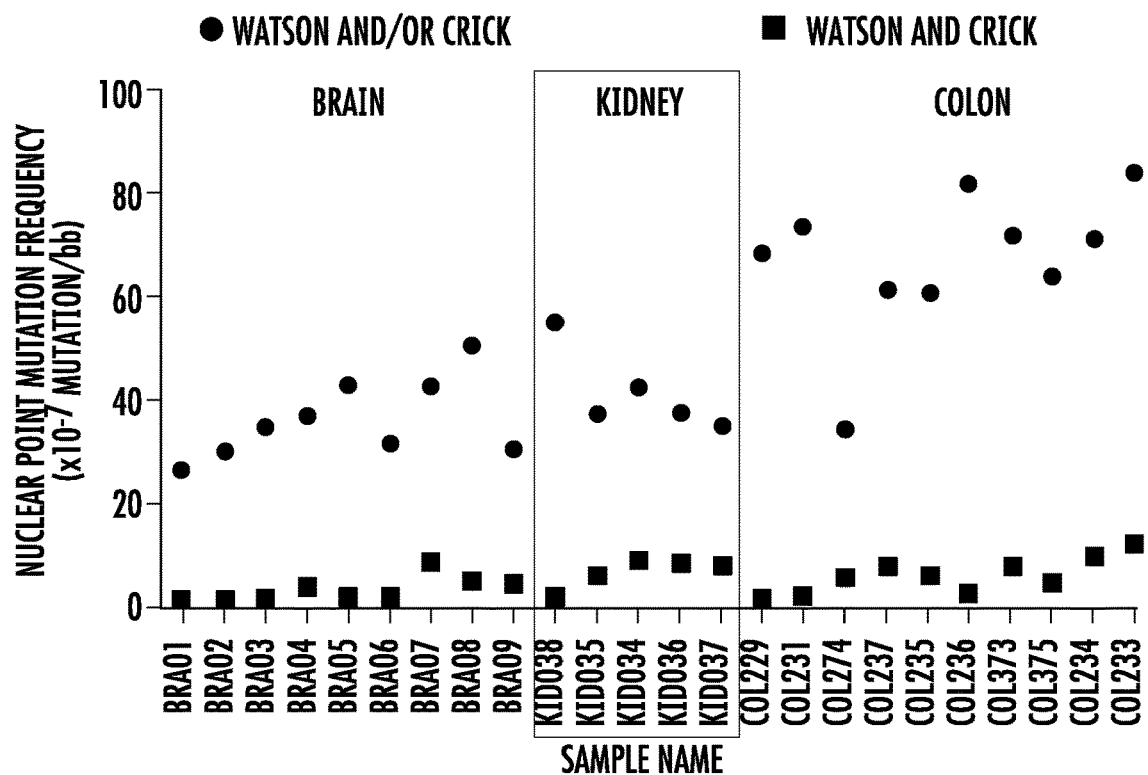
FIG. 6A-6B. Consideration of both Watson and Crick family members decreases artifacts, specifically G>T transversions.
Figure 6B:
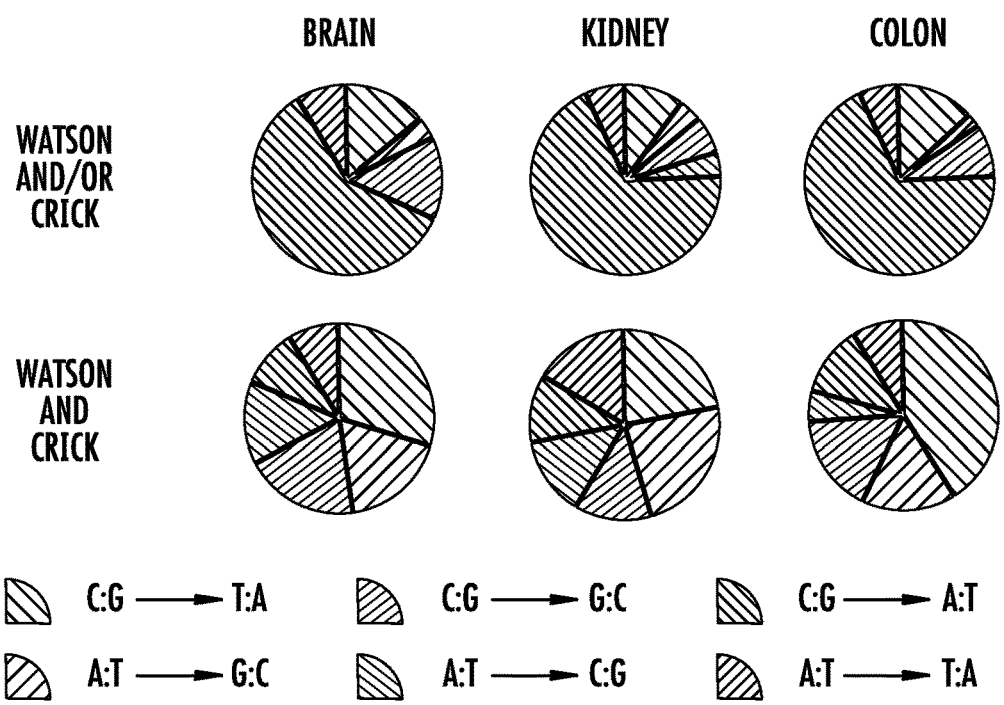

To identify rare, somatic mutations, it was necessary to eliminate germline and clonal variants from the BotSeqS data (we defined clonal as those present in both strands of more than one template molecule). We performed whole genome sequencing (WGS) of the same DNA sample or the same libraries that had been diluted for BotSeqS for 32 of the 34 individuals in this study (Supplementary Table 1, available online in the Proceedings of the National Academy of Sciences of the United States of America journal, Hoang et al., 113(35) PROC. NATL. ACAD. SCI. USA 9846-51 (2006) (doi: 10.1073/pnas. 1607794113). For the remaining two individuals (COL238 and COL239), Sanger sequencing was performed to eliminate clonal variants, demonstrating that WGS was not necessary for BotSeqS. The vast majority (median 92%, range 88-94%) of variants were found to be germline, easily identifiable from the matched WGS dataset. In addition to clonality, we eliminated potential artifacts by considering only well-mapped positions and by using other filters (Supplementary Tables 2-6 (available online in the Proceedings of the National Academy of Sciences of the United States of America journal, Hoang et al., 113(35) PROC. NATL. ACAD. SCI. USA 9846-51 (2006) (doi: 10.1073/pnas.1607794113) and Example 1). The requirement for mutations to be present on both strands was indeed necessary because, in the absence of this filter, there was a large number of G>T transversions (FIG. 6), known to represent artifacts in NGS library preparations[21]. We further performed a "spike-in" validation experiment by mixing one individual's normal DNA (PEN93) into another individual's normal DNA (PEN95) at two different ratios. Using BotSeqS, we were able to detect PEN93-specific SNPs in both samples with a 7.4-fold difference in frequency between the low and high spike-ins, within the expected error of the intended 10-fold difference (see Example 1).

From the 44 BotSeqS libraries, we identified a total of 666 and 876 rare somatic point mutations in mtDNA and nuclear DNA, respectively (Supplementary Tables 7 and 8, available online in the Proceedings of the National Academy of Sciences of the United States of America journal, Hoang et al., 113(35) PROC. NATL. ACAD. SCI. USA 9846-51 (2006) (doi: 10.1073/pnas.1607794113). All rare mutations passed visual inspection and a subset was Sanger-sequenced to confirm that the mutations were not germline or highly prevalent in the samples evaluated (see Example 1). As expected from previous studies, point mutation frequencies of mtDNA ($1.40 \pm 1.29 \times 10^{-5}$ mutation/bp, mean±s.d.) were significantly higher than those of nuclear DNA ($5.23 \pm 3.47 \times 10^{-7}$) in 25 control individuals (two-tailed t-test, P<0.0001; Supplementary Table 9, available online in the Proceedings of the National Academy of Sciences of the United States of America journal, Hoang et al., 113(35) PROC. NATL.

ACAD. SCI. USA 9846-51 (2006) (doi: 10.1073/pnas.1607794113). We further determined the specificity of BotSeqS using discordant germline heterozygous calls to estimate a false positive rate of $2.58 \times 10^{-12}$ (see Example 1).

Example 5

Mutation Frequencies Vary with DNA Repair Capacity and Carcinogen Exposure.

We first asked if BotSeqS can detect the elevated levels of mutations in the normal tissues of mismatch repair deficient individuals. Individuals with biallelic inactivating germline mutations in mismatch repair machinery show higher levels of mutation in both normal and tumor tissues[22, 23]. Therefore, we tested DNA from normal colon epithelium of individuals (COL238 and COL239) with biallelic germline inactivating mutations in the Post Meiotic Segregation 2 (PMS2) gene. Using BotSeqS, we found that the average mutation frequency of nuclear DNA in these two siblings ($6.63 \pm 3.47 \times 10^{-5}$ mutations/bp; ages 16 and 18) was significantly higher than that in similarly aged individuals ($5.13 \pm 1.73 \times 10^{-7}$ for COL235, COL236, COL237, COL374; average age 24) with proficient mismatch repair (two-tailed t-test, P<0.05, FIG. 2A). This 129-fold increase in nuclear mutation frequency was associated with a significant difference in the nuclear mutational spectrum between PMS2$^{+/+}$ and PMS2$^{-/-}$ cohorts (Fisher's exact test, P=0.04, FIG. 2B).

Figure 2A:
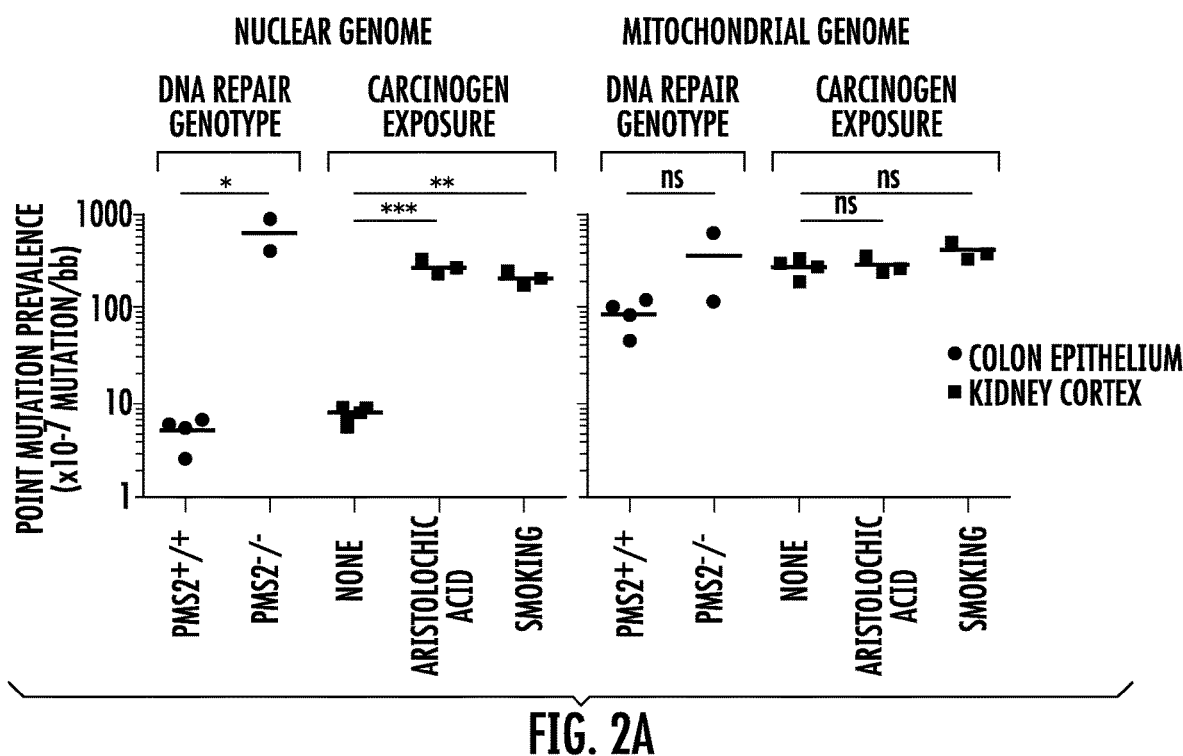
FIG. 2A-2B. Nuclear point mutations increase in normal tissues from individuals with defects in DNA repair or with exposure to environmental carcinogens compared to controls.
Figure 2B:
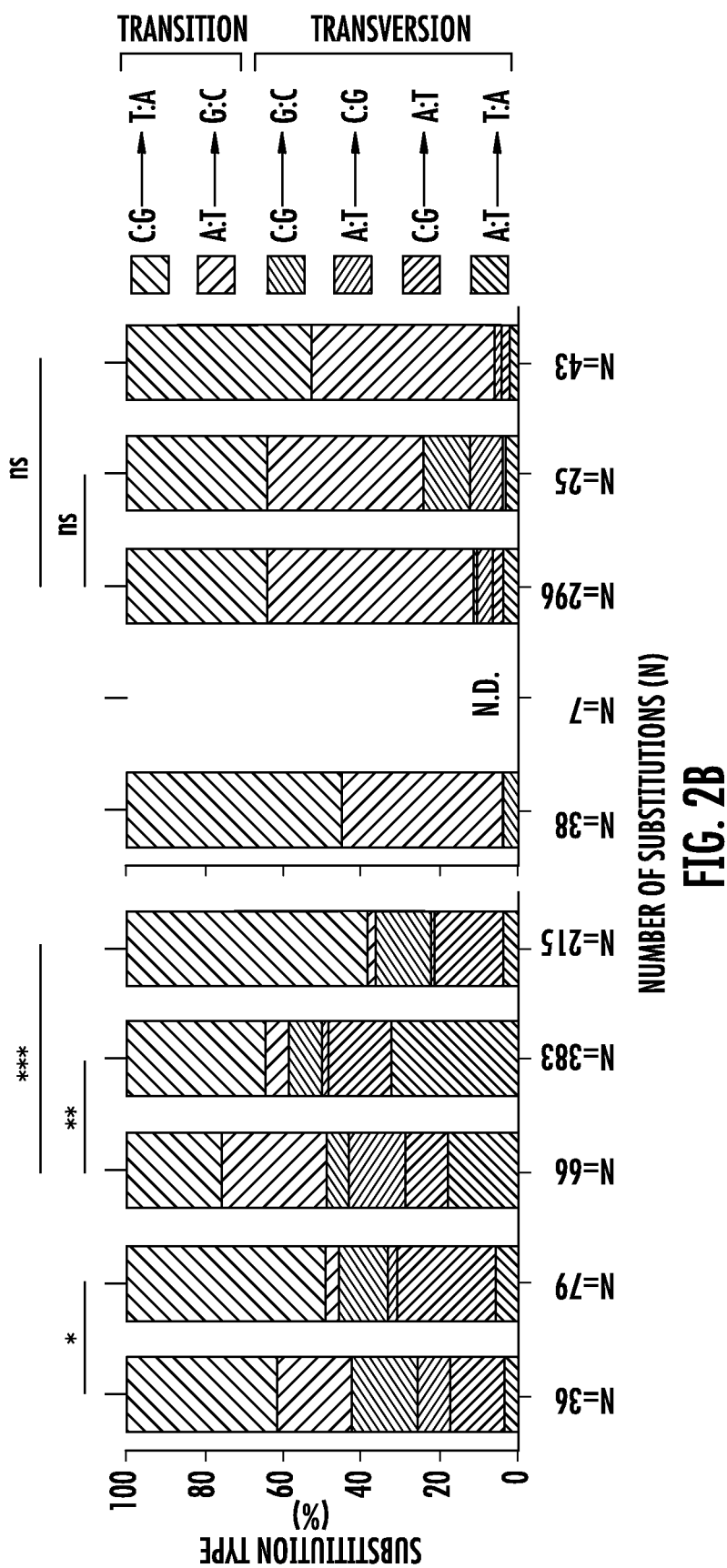

We also tested if BotSeqS could identify a high number of mutations in the normal tissues of individuals exposed to environmental carcinogens. We previously performed genome-wide sequencing of upper tract urothelial carcinomas, representing a cancer type associated with exposure to aristolochic acid (AA) or smoking[24]. Mutagens in tobacco smoke as well as AA are metabolized to form DNA-adducts in the normal kidney cortex[24, 25]. We compared four age-matched normal kidney cortices from individuals (KID034, KID035, KID036, KID037; average age 64 years) without known exposure to tobacco smoke or to AA with the normal kidney cortex of three heavy smokers (SA_117, SA_118, SA_119; average age 65 years) as well as with three individuals who had been exposed to AA (AA_105, AA_124, AA_126; average age 79 years). The nuclear point mutation frequencies in smokers and AA-exposed kidneys were significantly higher, by 27- and 36-fold, respectively, than in the non-exposed controls (one-way ANOVA with Bonferroni multiple comparison post-test, P<0.0001 for AA and P<0.001 for smoking) (FIG. 2A). This increased number of mutations in the nuclear genome was associated with a significantly altered nuclear mutational spectrum (Fisher's exact test with Bonferroni multiple comparison correction, $P=2.58 \times 10^{-8}$ for AA and $P=1.51 \times 10^{-15}$ for smoking) (FIG. 2B). Interestingly, the mtDNA point mutation frequencies and spectra between the non-exposed and exposed groups were not significantly different, despite the dramatic difference in their nuclear genomes (FIG. 2A, 2B).

Example 6

Rare Mutations Accumulate with Age.

Many lines of evidence indicate that the human body accumulates random mutations with age. BotSeqS was designed to directly measure differences such as these and we tested whether rare point mutation frequencies in the DNA of three normal human tissues were dependent upon age. Normal colonic epithelium from 11 individuals showed mutation frequencies that significantly increased with age, by an average of 30-fold in mtDNA and 6.1-fold in nuclear DNA, over 91 years (FIG. 3 and Table 1; one-way ANOVA with Bonferroni multiple comparison post-test, P<0.001 for both). Similarly, mutation frequencies increased by an average of 19-fold in mtDNA and 6.5-fold in nuclear DNA over 64 years in normal kidney cortices. The mutation frequencies in brain frontal cortex also significantly increased with age, albeit more slowly, by 7.3-fold in mtDNA and 5.7-fold in nuclear DNA over 90 years (one-way ANOVA with Bonferroni multiple comparison post-test, P<0.001 for mtDNA and P<0.05 for nuclear).

Figure 7:
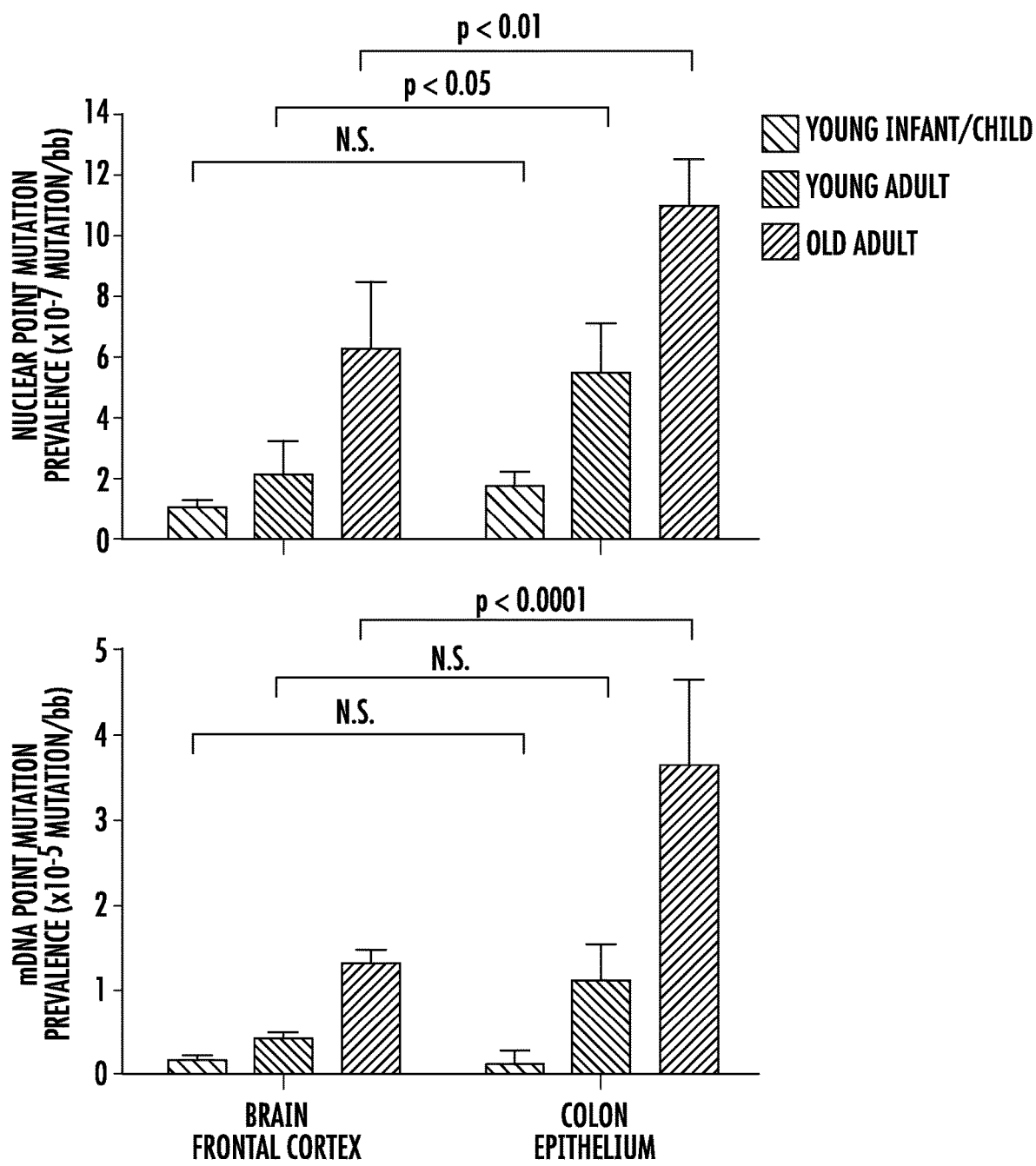
FIG. 7. Rare point mutations accumulate in normal tissues of the colon more than in brain. Point mutation frequency (y-axis) in nuclear (top graph) and mitochondrial (bottom graph) genome in normal brain frontal cortex (left side) and normal colon epithelium (right side) grouped by age (young infant/child in green, young adult in purple, old adult in blue). Averages of each age cohort are shown with error bars representing the standard deviations. Two-way ANOVA with Bonferroni multiple comparison post-test was performed using GRAPHPAD PRISM™ 5.0f software with P values reported above bars. n.s. (not significant) indicates P>0.05. For brain, the number of individuals and average age of group are as follows-infant/child: n=3, 3.5 years old (y/o) (BRA01, BRA02, BRA03); young adult: n=3 individuals, 22 y/o (BRA04, BRA05, BRA06); and old adult: n=3, 93 y/o (BRA07, BRA08, BRA09). For colon, infant/child: n=2, 5.5 y/o (COL229, COL231); young adult: n=6, 28 (COL235, COL236, COL237, COL373, COL374, COL375); old adult: n=3, 96 y/o (COL232, COL233, COL234).

Within our dataset, we could directly compare point mutation frequencies in brain versus colonic tissues in three different age groups (children <10 years; adults between 20 and 40 years; and old adults ≥90 years). Interestingly, the nuclear mutation frequency in colon was not significantly different from that of the brain in children ($1.81 \pm 0.45 \times 10^{-7}$ in colon vs. $1.06 \pm \times 10^{-7}$ in brain, two-way ANOVA with Bonferroni multiple comparison post-test, P>0.05). However, the mutation frequency in the colon was significantly higher than that of the brain in young adults ($5.51 \pm 1.62 \times 10^{-7}$ in colon vs. $2.16 \pm 1.11 \times 10^{-7}$ in brain, two-way ANOVA with Bonferroni multiple comparison post-test, P<0.05) as well as in old adults ($1.10 \pm 0.15 \times 10^{-6}$ in colon vs. $6.29 \pm 2.31 \times 10^{-7}$ in brain, two-way ANOVA with Bonferroni multiple comparison post-test, P<0.01) (FIG. 7). No significant differences were found between the mtDNA mutation frequency of the colon versus that of brain in relatively young individuals (children or young adults). However, the mtDNA mutation frequency in the colon was significantly higher than that of the brain in old individuals ($3.65 \pm 1.03 \times 10^{-5}$ in colon vs. $1.31 \pm 0.18 \times 10^{-5}$ in brain, two-way ANOVA with Bonferroni multiple comparison post-test, P<0.0001) (FIG. 7).

Example 7

The Mutational Patterns in mtDNA are Very Different from Those of Nuclear DNA.

We examined the spectra of the rare point mutations in each normal tissue studied. Mutations in mtDNA were dominated by transitions (97% in colon, 89% in kidney, and 91% in brain) with a heavy strand bias, as expected from previous studies[12] (FIG. 3 and Supplementary Table 7, available online in the Proceedings of the National Academy of Sciences of the United States of America journal, Hoang et al., 113(35) PROC. NATL. ACAD. SCI. USA 9846-51 (2006) (doi: 10.1073/pnas. 1607794113 The ratio of transitions to transversions was strikingly different in mtDNA (average of 15.3) compared to nuclear DNA (average of 1.1) in all three tissues.

Figure 8:
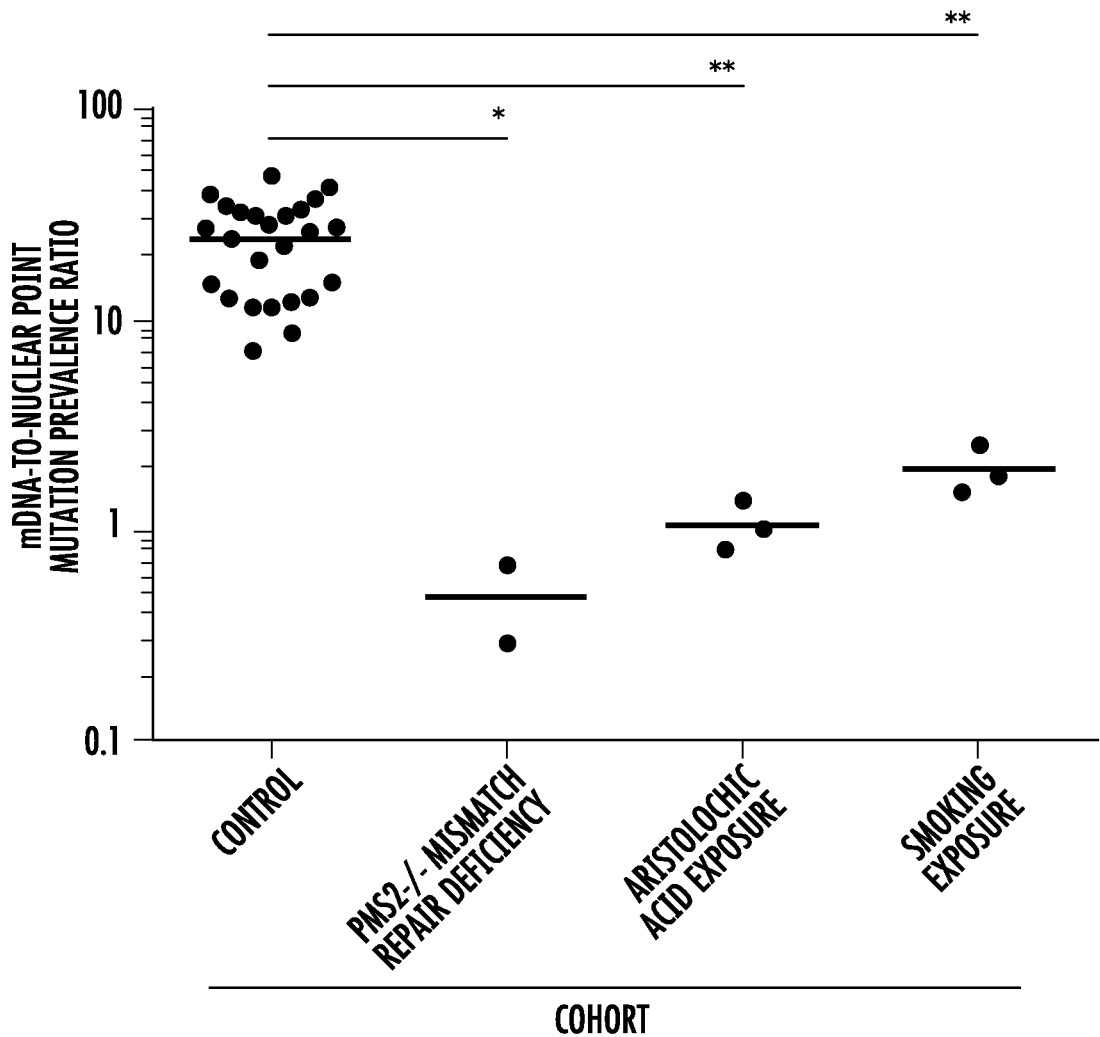
FIG. 8. Mitochondrial and nuclear point mutation frequencies in normal tissues from the same individual. Data points represent the ratio between mitochondrial to nuclear point mutation frequencies (y-axis) within the normal tissue of the same individual. Individuals were grouped into four cohorts (x-axis) with n=24 individuals for Control (see Supplementary Table 9), n=2 individuals (COL238, COL239) for DNA repair defect $PMS2^{-/-}$, n=3 individuals (AA_105, AA_124, AA_126) for aristolochic acid exposure, and n=3 individuals (SA_117, SA_118, SA_119) for smoking exposure. One ratio from the control cohort (COL229) was zero and omitted from this analysis. Average (red line) ratio for each cohort is 24.5 for Control, 0.5 for DNA repair defect $PMS2^{-/-}$, 1.1 for aristolochic acid exposure, and 2.0 for smoking exposure. *P<0.05, **P<0.01, one-way ANOVA with Bonferroni multiple comparison post-test.

To further assess the differences in mutation frequencies between the two genomes, we calculated the ratio between mtDNA-to-nuclear mutation frequencies for each individual (Supplementary Table 9, available online in the Proceedings of the National Academy of Sciences of the United States of America journal, Hoang et al., 113(35) PROC. NATL. ACAD. SCI. USA 9846-51 (2006) (doi: 10.1073/pnas. 1607794113). Point mutation frequencies in the mtDNA were on average 24.5-fold higher than the nuclear genome in normal tissues (control cohort, FIG. 8). In patients with exposure histories or DNA repair defects, the ratios were significantly smaller due to the concomitantly greater number of nuclear (but not mitochondrial) DNA mutations in such individuals compared to those from the control cohort (one-way ANOVA with Bonferroni multiple comparison post-test, P<0.05) (FIG. 8).

Example 8

Mutational Spectra are Tissue-Specific.

Figure 3:
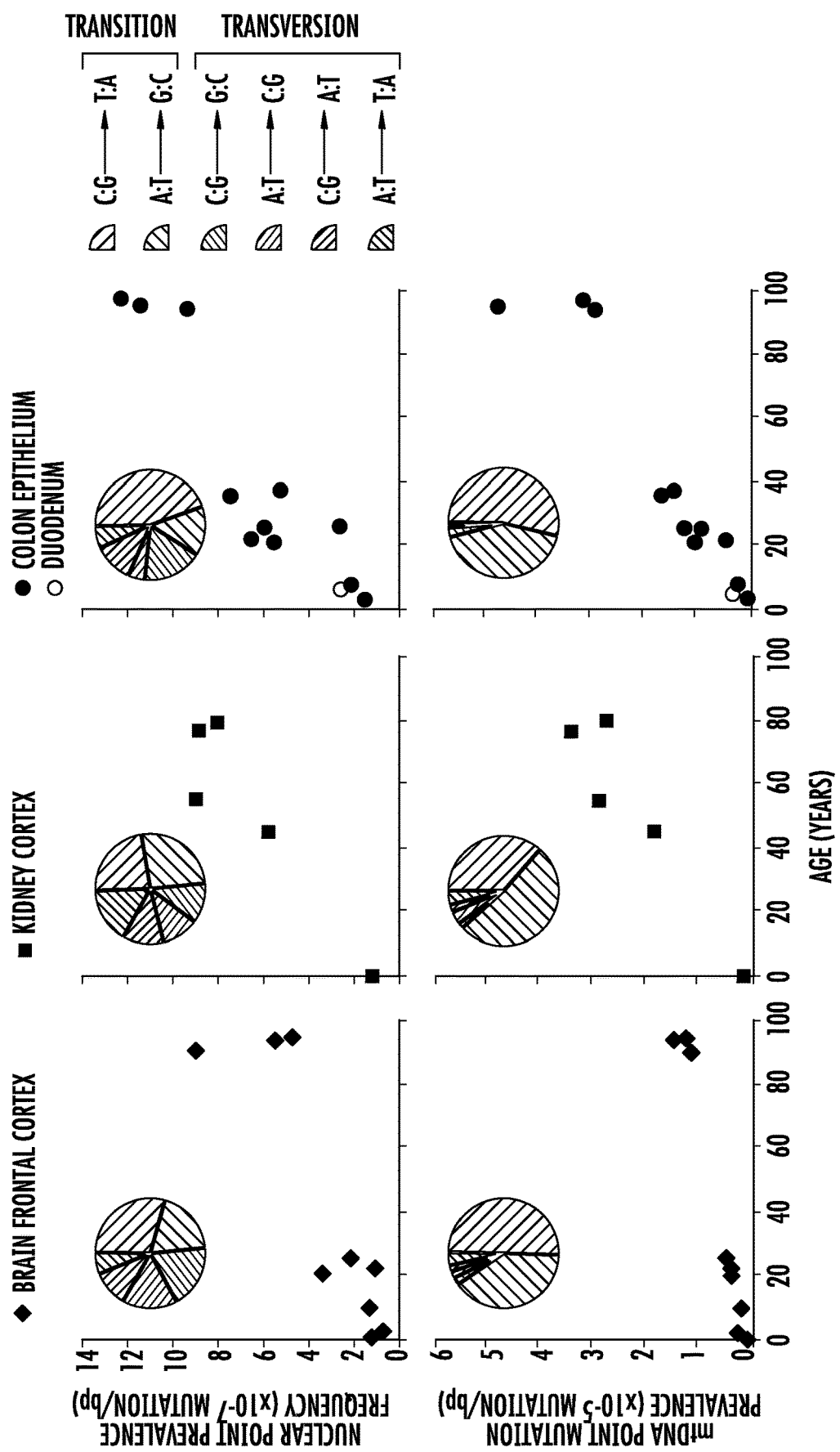
FIG. 3. Normal human tissues accumulate point mutations over a lifetime with genome-specific and tissue-specific mutational spectra. Point mutation frequencies in nuclear (top scatter plots) and mitochondrial (bottom scatter plots) genome measured in four normal tissue types (brain frontal cortex of 9 individuals, kidney cortex of 5 individuals, colon epithelium of 11 individuals, and duodenum of 1 individual). Twenty-six total individuals were assessed with each individual contributing to one normal tissue type. Pie chart insets show the frequencies of each substitution out of the six possible substitution types (see pie chart legend, right side). Each pie chart was compiled from the individuals represented in their respective scatter plots, with the exception that duodenum was omitted. The number of substitutions generating the pie charts for the nuclear genome was n=31 for brain, n=73 for kidney, n=94 for colon and for the mitochondrial genome was n=181 for brain, n=299 for kidney, n=116 for colon.

Though rare mutations in mtDNA are dominated by transitions, there are still tissue-specific mtDNA differences that can be appreciated from the pie charts in FIG. 3. For example, mitochondrial C:G to T:A transitions were more prominent, and A:T to G:C transitions less prominent, in normal colon (54% and 42%, respectively) and brain (51% and 40%, respectively) compared to normal kidney tissues (36% and 53%, respectively). The mutation spectra in the nuclear DNA of all three tissues were much more diverse. For example, C:G to T:A transitions predominated in normal colon (44% in colon compared to 22% in kidney and 29% in brain), while normal kidney and brain harbored a proportionately greater fraction of A:T to G:C transitions (25% in kidney and 19% in brain compared to 15% in colon) as well as A:T to C:G transversions (12% in kidney and 16% in brain compared to 5% in colon). Moreover, A:T to T:A transversions were more frequent in kidney (16%) compared to colon (6%) and brain (6%). Pairwise comparisons of the mutational spectra within each genome revealed significant differences between the substitution pattern of kidney and colon (Fisher's exact test with Bonferroni multiple comparison correction, P=0.0029 in mtDNA and P=0.0312 in nuclear DNA).

Figure 9A:
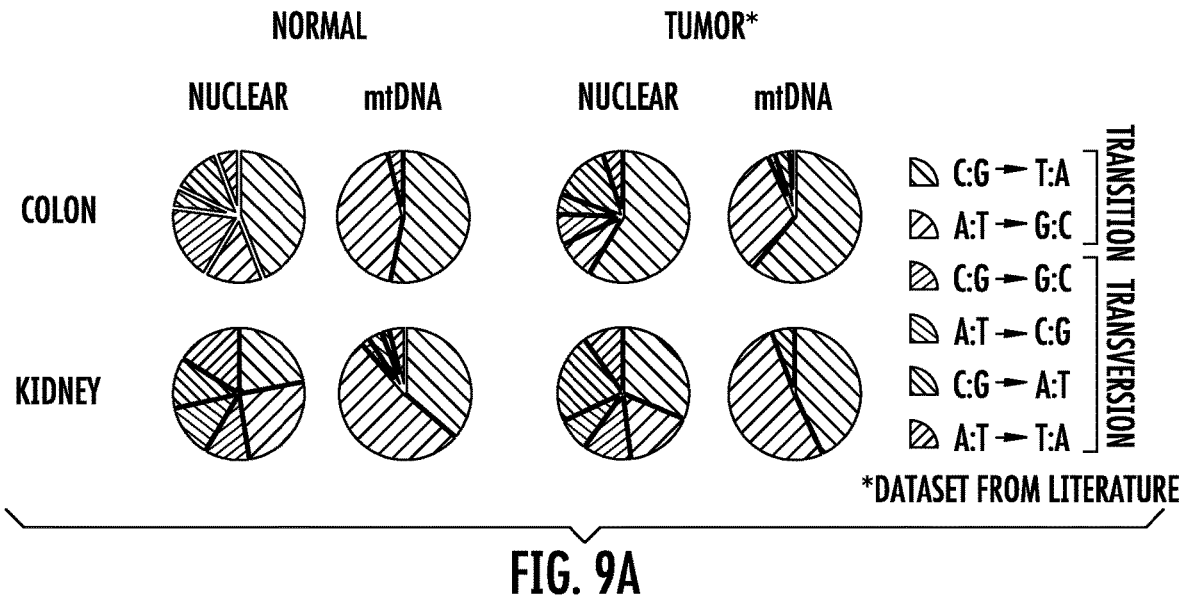
FIG. 9A-9B. Normal tissues and tumors derived from the same tissue type have similar mutation spectra (FIG. 9A) Pie charts of nuclear and mitochondrial frequencies of each substitution out of the six possible substitution types (see legend) comparing normal (left side) and tumors (right side) derived from colon (top) and kidney (bottom). "Normal" represents the rare mutational spectra data derived from normal tissues shown in FIG. 3. "Nuclear tumor mutations" represent clonal mutation data from colorectal carcinomas (COAD/READ) or clear cell renal carcinoma (KIRC) from the TCGA dataset #!Synapse:syn1729383 found at the synapse website. "mtDNA tumor mutations" from colon and kidney were acquired from "colorectal" and "renal" tumor types in supplementary file 2 of Ju et al., 2014. For normal tissues, the number of substitutions assessed was as follows: colon nuclear n=94 from 13 individuals, colon mtDNA n=116 from 12 individuals, kidney nuclear n=73 from 7 individuals, and kidney mtDNA n=299 from five individuals. For tumor tissue, the number of substitutions assessed was as follows: colorectal carcinoma nuclear n=18,538 from 193 individuals, colorectal carcinoma mtDNA n=64 from 76 individuals, clear cell renal cell carcinoma nuclear n=24,559 from 417 individuals, and renal carcinoma mtDNA n=16 from 23 individuals.
Figure 9B:
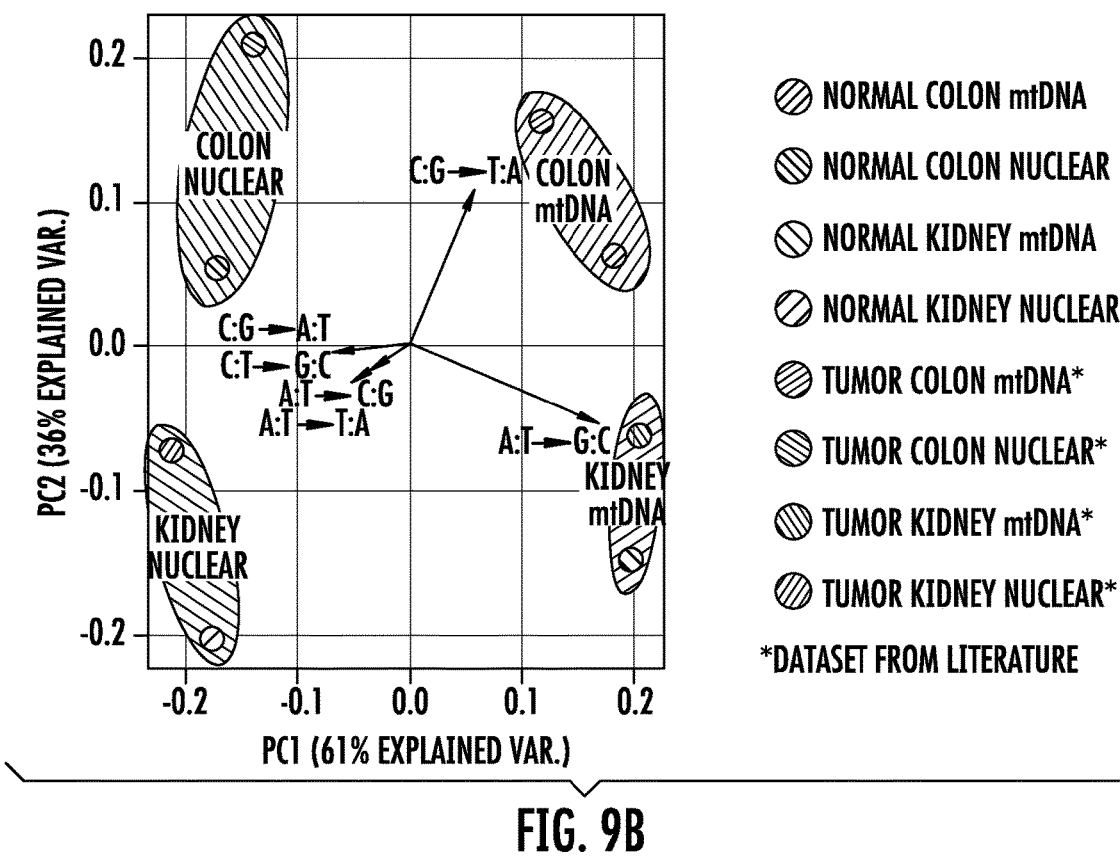

We compared the spectra of the rare mutations found in normal kidney and colon tissues to the clonal DNA mutations in cancers derived from the cells of these organs, using publically available data for the latter[26, 27]. Brain frontal cortex was excluded in this analysis because it was not clear what tumor type should be used for comparison. To search for similarities and differences among normal and tumor mutational spectra, principal component analysis was performed on the nuclear and mtDNA spectra derived from the data on normal kidney cortex, normal colon epithelium, clear cell renal carcinoma, and colorectal carcinoma. We found that the spectra of the rare mutations in normal colon and kidney tissues were very similar to those of the corresponding cancer type (FIG. 9).

REFERENCES

The disclosure of each reference cited is expressly incorporated herein.
1. Stratton, M. R., Campbell, P. J. & Futreal, P. A. The cancer genome. Nature 458, 719-724 (2009).
2. Kennedy, S. R., Loeb, L. A. & Herr, A. J. Somatic mutations in aging, cancer and neurodegeneration. Mech Ageing Dev 133, 118-126 (2012).
3. Vijg, J. Somatic mutations, genome mosaicism, cancer and aging. Current opinion in genetics & development 26, 141-149 (2014).
4. Ross, M. G. et al. Characterizing and measuring bias in sequence data. Genome biology 14, R51 (2013).
5. Albertini, R. J., Nicklas, J. A., O'Neill, J. P. & Robison, S. H. In vivo somatic mutations in humans: measurement and analysis. Annu Rev Genet 24, 305-326 (1990).
6. Cole, J. & Skopek, T. R. International Commission for Protection Against Environmental Mutagens and Carcinogens. Working paper no. 3. Somatic mutant frequency, mutation rates and mutational spectra in the human population in vivo. Mutat Res 304, 33-105 (1994).
7. Navin, N. et al. Tumour evolution inferred by single-cell sequencing. Nature 472, 90-94 (2011).
8. Zong, C., Lu, S., Chapman, A. R. & Xie, X. S. Genome-wide detection of single-nucleotide and copy-number variations of a single human cell. Science 338, 1622-1626 (2012).
9. Wang, J., Fan, H. C., Behr, B. & Quake, S. R. Genome-wide single-cell analysis of recombination activity and de novo mutation rates in human sperm. Cell 150, 402-412 (2012).
10. Kinde, I., Wu, J., Papadopoulos, N., Kinzler, K. W. & Vogelstein, B. Detection and quantification of rare mutations with massively parallel sequencing. Proceedings of the National Academy of Sciences of the United States of America 108, 9530-9535 (2011).
11. Jabara, C. B., Jones, C. D., Roach, J., Anderson, J. A. & Swanstrom, R. Accurate sampling and deep sequencing of the HIV-1 protease gene using a Primer ID. Proceedings of the National Academy of Sciences of the United States of America 108, 20166-20171 (2011).
12. Schmitt, M. W. et al. Detection of ultra-rare mutations by next-generation sequencing. Proceedings of the National Academy of Sciences of the United States of America 109, 14508-14513 (2012).
13. Hiatt, J. B., Pritchard, C. C., Salipante, S. J., O'Roak, B. J. & Shendure, J. Single molecule molecular inversion probes for targeted, high-accuracy detection of low-frequency variation. Genome research 23, 843-854 (2013).
14. Baslan, T. & Hicks, J. Single cell sequencing approaches for complex biological systems. Current opinion in genetics & development 26, 59-65 (2014).
15. Kivioja, T. et al. Counting absolute numbers of molecules using unique molecular identifiers. Nature methods 9, 72-74 (2012).
16. Kinde, I. et al. Evaluation of DNA from the Papanicolaou test to detect ovarian and endometrial cancers. Science translational medicine 5, 167ra164 (2013).
17. Kumar, A. et al. Deep sequencing of multiple regions of glial tumors reveals spatial heterogeneity for mutations in clinically relevant genes. Genome biology 15, 530 (2014).
18. Keys, J. R. et al. Primer ID Informs Next-Generation Sequencing Platforms and Reveals Preexisting Drug Resistance Mutations in the HIV-1 Reverse Transcriptase Coding Domain. AIDS Res Hum Retroviruses 31, 658-668 (2015).
19. Kennedy, S. R., Salk, J. J., Schmitt, M. W. & Loeb, L. A. Ultra-sensitive sequencing reveals an age-related increase in somatic mitochondrial mutations that are inconsistent with oxidative damage. PLoS Genet 9, e1003794 (2013).
20. Schmitt, M. W. et al. Sequencing small genomic targets with high efficiency and extreme accuracy. Nature methods 12, 423-425 (2015).
21. Costello, M. et al. Discovery and characterization of artifactual mutations in deep coverage targeted capture sequencing data due to oxidative DNA damage during sample preparation. Nucleic acids research 41, e67 (2013).
22. Parsons, R. et al. Mismatch repair deficiency in phenotypically normal human cells. Science 268, 738-740 (1995).
23. Shlien, A. et al. Combined hereditary and somatic mutations of replication error repair genes result in rapid onset of ultra-hypermutated cancers. Nature genetics 47, 257-262 (2015).

24. Hoang, M. L. et al. Mutational signature of aristolochic acid exposure as revealed by whole-exome sequencing. Science translational medicine 5, 197ra102 (2013).
25. Randerath, E. et al. Covalent DNA damage in tissues of cigarette smokers as determined by 32P-postlabeling assay. Journal of the National Cancer Institute 81, 341-347 (1989).
26. Ju, Y. S. et al. Origins and functional consequences of somatic mitochondrial DNA mutations in human cancer. eLife 3, (2014).
27. Kandoth, C. et al. Mutational landscape and significance across 12 major cancer types. Nature 502, 333-339 (2013).
28. Spalding, K. L., Bhardwaj, R. D., Buchholz, B. A., Druid, H. & Frisen, J. Retrospective birth dating of cells in humans. Cell 122, 133-143 (2005).
29. Lodato, M. A. et al. Somatic mutation in single human neurons tracks developmental and transcriptional history. Science 350, 94-98 (2015).
30. Madabhushi, R., Pan, L. & Tsai, L. H. DNA damage and its links to neurodegeneration. Neuron 83, 266-282 (2014).
31. Kennedy, S. R. et al. Detecting ultralow-frequency mutations by Duplex Sequencing. Nature protocols 9, 2586-2606 (2014).
32. Scheibye-Knudsen, M., Fang, E. F., Croteau, D. L., Wilson, D. M., 3rd & Bohr, V. A. Protecting the mitochondrial powerhouse. Trends in cell biology 25, 158-170 (2015).
33. Tomasetti, C. & Vogelstein, B. Cancer etiology. Variation in cancer risk among tissues can be explained by the number of stem cell divisions. Science 347, 78-81 (2015).
34. Tomasetti, C., Vogelstein, B. & Parmigiani, G. Half or more of the somatic mutations in cancers of self-renewing tissues originate prior to tumor initiation. Proceedings of the National Academy of Sciences of the United States of America 110, 1999-2004 (2013).
35. Hamilton, S. R. et al. The molecular basis of Turcot's syndrome. The New England journal of medicine 332, 839-847 (1995).
36. De Vos, M., Hayward, B. E., Picton, S., Sheridan, E. & Bonthron, D. T. Novel PMS2 pseudogenes can conceal recessive mutations causing a distinctive childhood cancer syndrome. American journal of human genetics 74, 954-964 (2004).
37. Jiao, Y. et al. DAXX/ATRX, MEN1, and mTOR pathway genes are frequently altered in pancreatic neuroendocrine tumors. Science 331, 1199-1203 (2011).
38. Li, H. Toward better understanding of artifacts in variant calling from high-coverage samples. Bioinformatics 30, 2843-2851 (2014).

We claim:
1. A method for sequencing DNA, comprising:
  a) fragmenting a double-stranded DNA population from an initial sample to form a library of double-stranded fragments, wherein said initial sample comprises a plurality of cells such that said library of double-stranded fragments are from a plurality of genomes from different cells;
  b) ligating adaptors to ends of at least a portion of the double-stranded fragments to form a library of double-stranded adaptor-ligated fragments;
  c) diluting at least a portion of the library of double-stranded adaptor-ligated fragments to form a diluted sample of double-stranded adaptor-ligated fragments;
  d) amplifying at least a portion of the double-stranded adaptor-ligated fragments in said diluted sample, to form a plurality of members from each single strand of the two strands of said double-stranded adaptor-ligated fragments that are amplified, such that a plurality of Watson families are formed from amplicons of one strand and a plurality of corresponding Crick families are formed from amplicons from the other strand, wherein the number of double-stranded adaptor-ligated fragments present in said diluted sample is such that, during said amplifying, less than 10 Watson families and corresponding Crick families are formed from said double-stranded adaptor-ligated fragments;
  e) sequencing at least two family members from one of said Watson families and at least two family members from one of said corresponding Crick families to obtain a nucleotide sequence for the sequenced members of the one Watson family and the one Crick family;

f) sequencing at least a portion of said double-stranded adaptor-ligated fragments from b) above, or sequencing at least a portion of said double-stranded fragments from a) above, thereby generating sequencing data comprising sequence information for germline and/or clonal mutations present in said plurality of genomes; and g) performing the following in silico with data analysis software:
   i) aligning the nucleotide sequence of said at least two members of said one Watson family to a reference sequence;
   ii) identifying a difference between at least 90% of the at least two members of said one Watson family and the reference sequence, wherein said difference is a single base difference, a two-base difference, a small insertion or deletion of 1 to 6 bases, or a substitution mutation;
   iii) identifying the difference as a potential rare or potential non-clonal somatic mutation if it is found in at least 90% of said nucleotide sequences of said at least two members of said one corresponding Crick family; and
   iv) performing either A) or B) below:
      A) identifying said potential rare or potential non-clonal somatic mutation as a rare or non-clonal somatic mutation when it is not present as a clonal and/or germline mutation in said sequencing data from said plurality of genomes, or
      B) identifying said potential rare or potential non-clonal somatic mutation as a clonal or germline mutation when it is present as a clonal and/or germline mutation in said sequencing data from said plurality of genomes.

2. The method of claim 1, wherein the difference is a single base difference.

3. The method of claim 1, wherein said at least two members of said one Watson family are at least 4 members of said one Watson family, and said at least two members of said one corresponding Crick family are at least 4 members of said one corresponding Crick family.

4. The method of claim 1, wherein the double-stranded DNA population comprises mitochondrial and/or nuclear DNA.

5. The method of claim 4, wherein the reference sequence comprises mitochondrial sequences.

6. The method of claim 1, wherein the adaptors are Y-shaped adaptors, having one end with complementary sequences and one end with non-complementary sequences.

7. The method of claim 1, wherein the adaptors are U-shaped or hairpin adaptors.

8. The method of claim 1, wherein the library of double-stranded adaptor-ligated fragments comprises fragments in which 5' and 3' ends are ligated to different adaptors.

9. The method of claim 1, wherein said at least two family members from said one Watson family are at least 10 members from said one Watson family, and said at least two members of said one corresponding Crick family are at least 10 family members from said one corresponding Crick family.

10. The method of claim 1, wherein the adaptors comprise random barcode sequences, and wherein the barcode sequences indicate a particular fragment among the double stranded adaptor-ligated fragments.

11. The method of claim 1, wherein said initial sample is from a human and is a sample selected from the group consisting of: plasma, stool, urine, and saliva.

* * * * *